(12) United States Patent
Cheng et al.

(10) Patent No.: US 12,116,498 B2
(45) Date of Patent: Oct. 15, 2024

(54) DURABLE PHOTOPOLYMERIZABLE CROSS-LINKED ANTI-FOULING COATINGS

(71) Applicant: UNIVERSITY OF IOWA RESEARCH FOUNDATION, Iowa City, IA (US)

(72) Inventors: Elise Lin Cheng, Iowa City, IA (US);
C. Allan Guymon, Iowa City, IA (US);
Marlan R. Hansen, Solon, IA (US);
Braden Leigh, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 18/507,969

(22) Filed: Nov. 13, 2023

(65) Prior Publication Data
US 2024/0084163 A1     Mar. 14, 2024

Related U.S. Application Data

(60) Continuation of application No. 18/079,085, filed on Dec. 12, 2022, now Pat. No. 11,814,526, which is a
(Continued)

(51) Int. Cl.
*C09D 133/10* (2006.01)
*A61L 27/16* (2006.01)
(Continued)

(52) U.S. Cl.
CPC ............ *C09D 133/10* (2013.01); *A61L 27/16* (2013.01); *A61L 27/34* (2013.01); *A61L 29/041* (2013.01);
(Continued)

(58) Field of Classification Search
None
See application file for complete search history.

(56) References Cited

U.S. PATENT DOCUMENTS

| 10,385,151 B2 | 8/2019 | Fukagawa |
| 2010/0145286 A1 | 6/2010 | Zhang et al. |

(Continued)

FOREIGN PATENT DOCUMENTS

| WO | 1996029370 | 3/1996 |
| WO | 2010065960 | 6/2010 |

(Continued)

OTHER PUBLICATIONS

China Patent Office, First Office Action, application No. 201780049849.x, issued Mar. 19, 2021, 14 pages.
(Continued)

*Primary Examiner* — Peter A Salamon
(74) *Attorney, Agent, or Firm* — McAndrews, Held & Malloy, Ltd.

(57) ABSTRACT

Durable, anti-fouling, crosslinked zwitterionic coatings that are grafted to the surface of a substrate through covalent bonding are disclosed. When exposed to a light source, zwitterionic monomers react with a crosslinker and with activated radicals at the surface of the substrate, simultaneously forming the crosslinked zwitterionic coating and anchoring it to the surface of the substrate. Photomasking techniques can be used to micropattern the zwitterionic coatings. The zwitterionic coatings can be applied to a variety of substrates, including medical devices and systems.

15 Claims, 27 Drawing Sheets

Related U.S. Application Data division of application No. 16/312,448, filed as application No. PCT/US2017/039153 on Jun. 24, 2017, now Pat. No. 11,525,069.

(60) Provisional application No. 62/354,527, filed on Jun. 24, 2016.

(51) Int. Cl.
| | |
|---|---|
| *A61L 27/34* | (2006.01) |
| *A61L 29/04* | (2006.01) |
| *A61L 29/08* | (2006.01) |
| *A61L 31/04* | (2006.01) |
| *A61L 31/10* | (2006.01) |
| *C08K 5/11* | (2006.01) |
| *C09D 5/16* | (2006.01) |
| *C09D 133/26* | (2006.01) |
| *C09D 151/08* | (2006.01) |

(52) U.S. Cl.
CPC ............ *A61L 29/085* (2013.01); *A61L 31/048* (2013.01); *A61L 31/10* (2013.01); *C08K 5/11* (2013.01); *C09D 5/1675* (2013.01); *C09D 133/26* (2013.01); *C09D 151/085* (2013.01); *A61L 2300/404* (2013.01); *A61L 2420/08* (2013.01)

(56) References Cited

U.S. PATENT DOCUMENTS

| | | |
|---|---|---|
| 2010/0152708 A1 | 6/2010 | Li et al. |
| 2011/0305872 A1 | 12/2011 | Li et al. |
| 2012/0322939 A1 | 12/2012 | Jiang et al. |
| 2015/0182673 A1 | 7/2015 | Delaney, Jr. et al. |
| 2015/0320913 A1 | 11/2015 | Song et al. |
| 2020/0308440 A1 | 10/2020 | Cheng et al. |

FOREIGN PATENT DOCUMENTS

| | | |
|---|---|---|
| WO | 2011057219 | 5/2011 |
| WO | 2011156589 | 12/2011 |
| WO | 2014085275 | 6/2014 |

OTHER PUBLICATIONS

Japan Patent Office, Reasons for Rejection, application No. 2018-567579, issued Mar. 25, 2021, 8 pages.
International Searching Authority, International Search Report and Written Opinion, application No. PCT/US2017/039153, dated Dec. 20, 2017, 24 pages.
China Patent Office, Second Office Action, application No. 201780049849.x, issued Dec. 14, 2021, 15 pages.
IP Australia, Examination Report, application No. 2017280359, Apr. 16, 2021, 4 pages.
European Patent Office, Communication pursuant to Article 94(3) EPC, Oct. 4, 2022, 7 pages.
European Patent Office, Communication pursuant to Article 94(3) EPC, Feb. 23, 2021, 7 pages.
Canada Patent Office, Office Action, Application No. 3,028,732 dated Sep. 26, 2023, 5 pages.
Official Communication, European Patent Application No. 17 740 822.6, dated May 2, 2024, 7 pages.

CBMA

SBMA

PEGDA

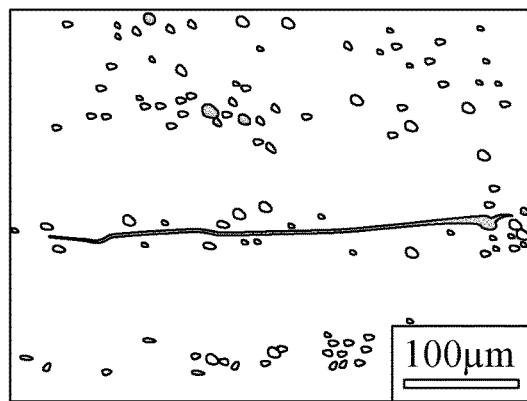
FIG. 7C
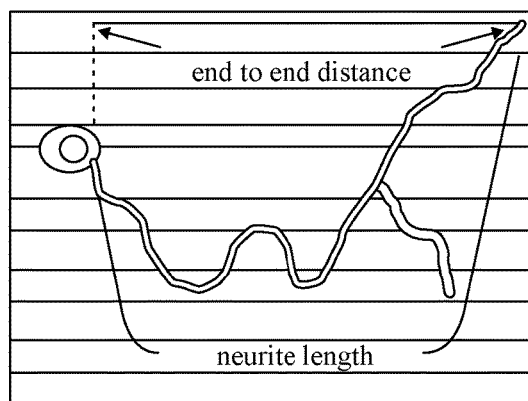 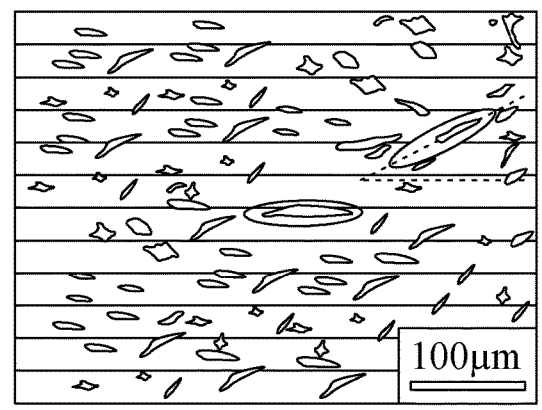
FIG. 8A          FIG. 8B

DURABLE PHOTOPOLYMERIZABLE CROSS-LINKED ANTI-FOULING COATINGS

RELATED APPLICATIONS

This application is a continuation of application Ser. No. 18/079,085, filed Dec. 12, 2022, which is a divisional of application Ser. No. 16/312,448, filed Dec. 21, 2018, under 35 U.S.C. 371 as a U.S. National Phase application of, and claims the benefit of priority to, International Patent application serial number PCT/US2017/039153, filed Jun. 24, 2017, which claims the benefit of priority to U.S. Provisional Patent application Ser. No. 62/354,527, filed Jun. 24, 2016. The entire text of each of the aforementioned applications is incorporated herein by reference in its entirety.

FEDERALLY SPONSORED RESEARCH OR DEVELOPMENT

This invention was made with government support under DC012578 and DC000040 awarded by the National Institutes of Health. The Government has certain rights in the invention.

FIELD OF THE INVENTION

The present embodiment relates to photo-grafting and photo-polymerization of antifouling surface coatings on polymers and metals, such as those used in medical and other devices, and specifically relates to durable photopolymerizable cross-linked anti-fouling surface coatings on such devices.

BACKGROUND

The phenomenon of biofouling is caused by the adsorption of biomolecules, microorganisms (such as bacteria), cells, and/or tissues to a surface.

Biofouling is a multistep process. Exposure of a surface or structure to biological surfaces, fluids or tissues results in the adsorption of a film of dissolved organic material, such as proteins. Subsequently, microorganisms, cells, or tissue can more readily adhere to the surface leading to inflammation, scarring, fibrosis or infection. In the case of bacterial infection of a foulable surface, colonies of bacteria appear and form a biofilm. As the attached bacterial cells begin to multiply, the biofilm thickens. As the process continues, additional colonies of organisms expand on the biofilm coated surfaces and secrete a compound thought to be a hydrophobic glycoprotein biological adhesive which allows these colonies of organisms to become firmly attached to a surface and resistant to most antimicrobials.

Biofouling represents a significant problem for many surfaces and structures and may result in interference with the normal use and condition of the surface or structure. Fouling can reduce function or longevity of the device. For example, protein deposition on a contact lens or within a spinal fluid shunt can limit the longevity and function of the device. Fouling of endoscopes, probes, and other devices requires frequent cleaning and sterilization. Fouling also increases susceptibility to infection with bacteria, yeast, or other micro-organisms. For example, many materials placed in the body are prone to bacterial infection such as orthopedic implants, vascular access lines, urinary catheters, among many others. Often these infections require revision surgery, prolonged antibiotic use, and even permanent removal of the device.

Further, fibrosis, inflammation, and scarring in response to implanted biomaterials represent a significant disadvantage to many medical implants. As one example, fibrosis to cochlear implant electrode arrays increases electrode resistance and channel interaction, reduces battery life, and leads to increased trauma to the cochlear tissues and poorer performance with the implant. All current implants have shown some degree of scar tissue formation. The increasing popularity of cochlear implant electrode arrays capable of preserving residual hearing has recently made these neural prostheses an option for patients with partial hearing loss. However, formation of scar tissue after cochlear implantation can be detrimental to residual hearing. In patients who have received a cochlear implant and initially retain some of their natural, acoustic hearing, subsequent hearing loss may be due, at least in part, to excess scar formation around the implant. As another example, fibrosis and scarring following placement of an intra-arterial stent can lead to restenosis.

Fouling of stents and catheters placed into arteries and veins can lead to increased thrombosis and platelet adhesion. Similarly, adhesion and activation of proteins and cells in medical devices and tubing (e.g., dialysis and heart-lung bypass machines) that require that blood products be manipulated outside of blood vessels can lead to thrombosis, platelet adhesion, and abnormal activation or death of blood cells.

Therefore, there is a need to address fouling of a substrate, such as biomolecule, bacteria, cell, or tissue adhesion to a medical device or a component of a medical device. Beyond medical devices, other items likewise suffer from biofouling, which may result in a reduction in function or longevity, or micro-organism adhesion. These devices could include household or industrial items like eating utensils, liquid containers, and storage containers. It could also include research laboratory equipment such as pipettes and tips, storage containers, and tubes (e.g., centrifuge and microcentrifuge) and plates.

Implantable biomedical devices such as implant electrodes and electrical prostheses can be implanted in the body to provide electrical stimulation to internal organs and tissues. For example, intra cochlear electrodes restore a sense of hearing by direct electrical stimulation of the neural tissue near an electrode contact. For most cochlear implant electrode arrays on the market today, insertion requires forces of sufficient degree that the electrode arrays can damage the delicate tissues in the cochlea. The required force to insert the implant electrode is related to various factors including the size, geometry, and number of electrode contacts, internal structure and the material used in the fabrication of the particular device. Material used in such devices includes materials for wires, contacts, functional metallic or polymer segments, and bulk material. The size of the implant electrode, the rigidity of the material used, the hydrophobicity of the outer shell of the electrode material, the energy stored in the electrode device and the insertion process of the device affect the amount and location of damage inflected on the tissue during electrode placement. In addition, removal and replacement of the system, or of particular parts of the system, may also cause trauma and damage to living tissue. It would be desirable to have an implant electrode material that is flexible and durable to minimize tissue damage, yet have anti-fouling and anti-fibrotic properties.

Polyethylene glycol and derivatives thereof have been used as anti-fouling agents. However, recent results demonstrate that polyethylene glycol networks, although bioinert, still enable some degree of fouling, fibrosis, and infection. Zwitterionic polymers have been used in recent years as an anti-fouling material. Zwitterionic materials containing intramolecular positive and negative charges have been shown to resist protein adsorption and fouling. The putative mechanism of action is that proximity of intramolecular positive and negative charges strongly affects the organization of surface water molecules in a hydrogen-bonded network, making adsorption of biomolecules energetically unfavorable.

While zwitterionic materials were originally developed for industrial applications, these materials were recently found to reduce tissue fibrosis. Studies in a mouse model have shown a decrease in the fibrotic capsule formation around subcutaneous zwitterionic bulk hydrogel implants. There has therefore been great interest in using zwitterionic materials in implantable and insertable devices, including urinary catheters and intravascular devices. However, zwitterionic hydrogels used as bulk materials are fragile and are not suitable for many applications.

Zwitterions have also been used as surface coatings, which have been shown to resist bacterial adhesion and biofilm formation. One approach has been to coat a substrate with an ungrafted zwitterionic hydrogel. These hydrogels are not covalently linked to the substrate and are prone to delamination. A second approach has been to coat a substrate by covalently grafting zwitterionic polymer brushes to the substrate using surface initiating techniques (e.g., surface initiated atom transfer radical polymerization). These zwitterionic brush coatings are very thin (e.g., less than 100 nm) and fragile, and are easily sheared off.

Therefore, bearing the above in mind, there remains the need to provide effective anti-biofouling polymer coatings which are durable for prolonged use.

SUMMARY

The present technology is directed to durable cross-linked zwitterionic coatings that are grafted to the surface of a substrate through covalent bonding. In some embodiments, the zwitterionic monomers, when exposed to a light source, react with a crosslinker and with activated radicals at the surface of the substrate to simultaneously form the cross-linked zwitterionic coating and anchor it to the substrate. This formation of the coating through photopolymerization confers the ability to create precisely micropatterned zwitterionic coatings using photomasking.

Accordingly, in one embodiment, a system is provided having a substrate and a cross-linked coating on the substrate. The cross-linked coating may include zwitterionic polymers or poly(ethylene)glycol. The cross-linked coating may be covalently bonded to at least one surface of the substrate and configured to resist the adhesion of biomolecules (e.g. protein, nucleic acid, sugars, lipids), cells, tissues, or bacteria to the substrate surface.

In another aspect, the disclosure provides a substrate having a copolymer covalently bonded to at least one surface of the substrate. The co-polymer may comprise repeating units having the following structure:

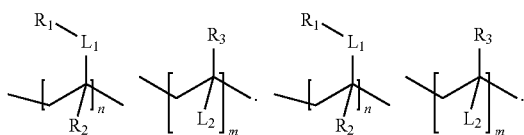

$R_1$ is a pendant group comprising a zwitterionic group; $R_2$, $R_3$ are each independently a hydrogen, substituted or unsubstituted alkyl, or alkyloxy; $L_1$ is a linking group; n and m may be the same or different and are each an integer; and $L_2$ is a cross-linking group.

In further embodiment, the present disclosure discloses a co-polymer. The co-polymer may comprise repeating units. The repeating units may have structures of:

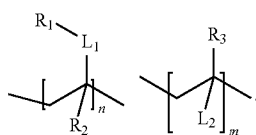

$R_1$ is a pendant group comprising a zwitterionic group; $R_2$, $R_3$ are each independently a hydrogen, substituted or unsubstituted alkyl, or alkyloxy; $L_1$ is a linking group; n and m may be the same or different and are each an integer; and $L_2$ is a cross-linking group.

In still another embodiment, the present disclosure provides a method for producing a coating on a substrate to inhibit adhesion by biomolecules, cells, tissues or bacteria. The substrate may be a component of a medical system. The method comprises pretreating the surface of the substrate with a process (e.g. plasma treatment) or substance (e.g. coupling agent) to promote adhesion of the coating to the substrate. Then a liquid that contains a zwitterionic monomer is applied to the surface of the substrate. The zwitterionic monomer is polymerized in the presence of a cross-linker under a light source to form a cross-linked zwitterionic polymer coating which is covalently bonded to the substrate surface.

In still another embodiment, the present disclosure provides a method for producing a coating on a substrate to inhibit adhesion by biomolecules, cells, tissues or bacteria. The substrate may be a component of a medical system. The method comprises pretreating the surface of the substrate with a type II hydrogen abstraction initiator to promote covalent bonding of the coating to the substrate. Then a liquid that contains a zwitterionic monomer is applied to the surface of the substrate. The zwitterionic monomer is polymerized in the presence of a crosslinker under a light source to form a zwitterionic polymer coating.

Additional features and advantages of the present technology are set forth in the detailed description, which follows, and in part are apparent to those skilled in the art from that description or recognized by practicing the embodiments described, including the detailed description, the claims, and the appended drawings.

It is to be understood that both the foregoing general description and the following detailed description describe various embodiments and provide an overview or framework for understanding the claimed subject matter. The accompanying drawings are included to provide a further understanding of the embodiments, and are incorporated into and constitute a part of this specification. The drawings illustrate the embodiments described, and with the description explain the principles and operations of the claimed subject matter.

BRIEF DESCRIPTION OF THE DRAWINGS

The following is a description of the figures in the accompanying drawings. The figures are not necessarily to scale, and certain features and certain views of the figures may be shown exaggerated in scale or in schematic in the interest of clarity or conciseness.

FIG. 7C illustrates primary spiral ganglion cells cultured on glass with a patterned CBMA coating.

FIG. 8A is a schematic representing the measurement of total neurite length ($T_L$) and the measurement of neurite aligned length ($A_L$) (i.e., the length of the neurite aligned in the pattern direction).

FIG. 8B illustrates Schwann cell alignment with a patterned coating determined by measuring the angle (θ) of an ellipse fitted to the major axis of the cell relative to the pattern.

DETAILED DESCRIPTION

Figure 1:
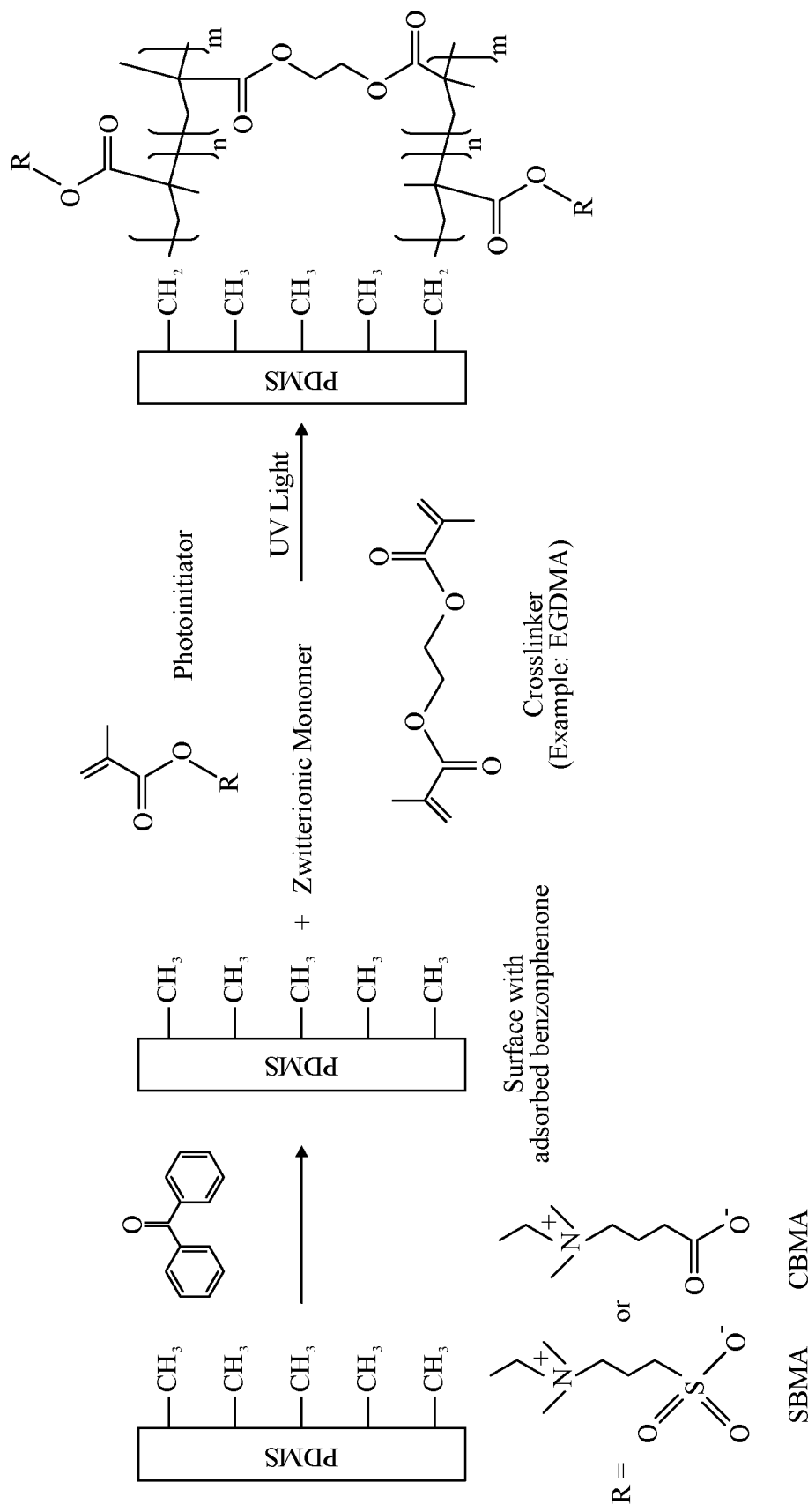
FIG. 1 is a schematic diagram illustrating one embodiment of a photo-chemical process for forming a durable anti-fouling zwitterionic coating on the surface of a PDMS substrate.

The present disclosure can be understood more readily by reference to the following detailed description, drawings, examples, and claims, and their previous and following description. However, before the present compositions, articles, devices, and methods are disclosed and described, it is to be understood this disclosure is not limited to the compositions, articles, devices, and methods disclosed, unless otherwise specified, and can vary. It is also to be understood that the terminology used is to describe particular aspects only and is not intended to be limiting.

The following description of the disclosure is provided as an enabling teaching of the disclosure in its known embodiments. Those skilled in the art will recognize and appreciate that many changes can be made to the aspects of the disclosure described, while still obtaining the beneficial results of the present disclosure. It will also be apparent that some of the desired benefits of the present disclosure can be obtained by selecting some of the features of the present disclosure without utilizing other features. Those who work in the art will recognize that many modifications and adaptations to the present disclosure are possible and can even be desirable in certain circumstances and are a part of the present disclosure. The following description is provided as illustrative of the principles of the present disclosure and not in limitation thereof.

Reference will now be made to the present preferred embodiment(s), examples of which are illustrated in the accompanying drawings. Using a particular reference character in the respective views indicates the same or like parts.

Unless otherwise indicated, all numbers expressing quantities of ingredients, properties such as size, weight, reaction conditions and so forth used in the specification and claims are to be understood as modified in all instances by the term "about". Unless indicated to the contrary, the numerical parameters in the following specification and attached claims are approximations that may vary depending upon the desired properties sought to be obtained by the invention. At the least, and not as an attempt to limit the application of the doctrine of equivalents to the claims, each numerical parameter should be construed in light of the number of reported significant digits and by applying ordinary rounding techniques, and should not be construed as showing all elements to scale.

Various inventive features are described below that can each be used independently of one another or in combination with other features.

Definitions

"Zwitterion" or "zwitterionic material" refers to a macromolecule, material, or moiety possessing both cationic and anionic groups. These charged groups are balanced, resulting in a material with zero net charge. Zwitterionic polymers may include both polyampholytes (e.g, polymers with the charged groups on different monomer units) and polybetaines (polymers with the anionic and cationic groups on the same monomer unit).

"Polymer", as used herein, includes homopolymers or copolymers.

"Co-polymer", as used herein, refers to any polymer composed of two or more different monomers.

As used herein, the term "hydrogel" refers to a material that is a polymer network having water as the swelling medium.

"Antimicrobial" as used herein, refers to molecules and/or compositions that inhibit the growth of (i.e., bacteriostatic), and/or prevent fouling by, microorganisms including bacteria, yeast, fungi, mycoplasma, viruses or virus infected cells, cancerous cells, and/or protozoa.

"Anti-thrombogenic", as used herein, refers to the ability of a material to resist thrombus formation.

"Adhesion", as used herein, refers to the non-covalent or covalent attachment of polymers, proteins, cells, or other substances to a surface.

"Bioactive agent" or "active agent" or "biomolecule", used here synonymously, refers to any organic or inorganic agent that actively or passively influences a biological system. For example, a bioactive agent can be an amino acid, peptide, antimicrobial peptide, immunoglobulin, an activating, signaling or signal amplifying molecule, including, but not limited to, a protein kinase, a cytokine, a chemokine, an interferon, tumor necrosis factor, growth factor, growth factor inhibitor, hormone, enzyme, receptor-targeting ligand, gene silencing agent, ambisense, antisense, an RNA, a living cell, cohesin, laminin, fibronectin, fibrinogen, osteocalcin, osteopontin, or osteoprotegerin. Bioactive agents can be proteins, glycoproteins, peptides, oligliopeptides, polypeptides, inorganic compounds, organometallic compounds, organic compounds or any synthetic or natural, chemical or biological compound.

"Anti-fouling", as used herein, means that the composition reduces or prevents the amount of adhesion of biomolecules, including blood proteins, plasma, cells, tissue and/or microorganisms, to the substrate relative to the amount of adhesion to a reference substrate such as a non-coated polyurethane surface. Preferably, a device surface is substantially anti-fouling in the presence of human blood. Preferably the amount of adhesion is decreased at least 20%, 25%, 30%, 35%, 40%, 45%, 50%, 55%, 60%, 65%, 70%, 75%, 80%, 85%, 90%, 95%, 99%, 99.5%, or 99.9% relative to the reference polymer. For mixed protein solutions, such as whole plasma, surface plasmon resonance (SPR) or optical waveguide light mode spectroscopy (OWLS) can be utilized to measure surface protein adsorption without necessitating the use of individual antigens for each protein present in solution. Additionally, radiolabeled proteins may be quantified on the surface after adsorption from either one protein or complex mixtures.

"Brush" or "Polymer Brush" are used herein synonymously and refer to individual polymer chains that are bound to a surface generally through a single point of attachment. The polymers can be end-grafted (attached via a terminal group) or attached via a side chain or a position in the polymer chain other than a terminal position. The polymers can be linear or branched. For example, the polymer chains described herein can contain a plurality of side chains that contain anti-fouling groups. The side chains can consist of a single anti-fouling moiety or monomer and/or a anti-fouling oligomer (e.g., 2-10 monomers) or polymer (e.g., >10 monomers).

"Density", as used herein, refers to the mass of material including, but not limited to, anti-fouling materials and bioactive agents, that is immobilized per surface area of substrate.

As used herein, the term 'about' will be understood by persons of ordinary skill in the art and will vary to some extent on the context in which is used. If there are uses of the term which are not clear to persons of ordinary skill in the art given the context in which is used, 'about' will mean up to plus or minus 20% of the particular term.

"Hydrophilic" refers to polymers, materials, or functional groups which have an affinity for water. Such materials typically include one or more hydrophilic functional groups, such as hydroxyl, zwitterionic, carboxyl, amino, amide, phosphate, hydrogen bond forming, and/or ether groups.

The term "alkyl" refers to the radical of saturated or unsaturated aliphatic groups, including straight-chain alkyl, alkene, and alkyne groups, branched alkyl, alkene, or alkyne groups, cycloalkyl(alicyclic), cycloalkene, and cycloalkyne groups, alkyl, alkene, or alkyne substituted cycloalkyl, cycloalkene, or cycloalkyne groups, and cycloalkyl substituted alkyl, alkene, or alkyne groups. In preferred embodiments, a straight chain or branched chain alkyl has 30 or fewer carbon atoms in its backbone (e.g., C1-C30 for straight chain, C3-C30 for branched chain), preferably 20 or fewer carbons, more preferably less than 10 carbons atoms, most preferably less than 7 carbon atoms. Likewise, preferred cycloalkyls have from 3-10 carbon atoms in their ring structure, and more preferably have 5, 6 or 7 carbons in the ring structure.

The term "alkoxy" or "alkyloxy" refers to an alkyl group singularly bonded to oxygen.

It should be understood that "substitution" or "substituted" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. The polymers described herein are not intended to be limited in any manner by the permissible substituents of organic compounds.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, but are not limited to, aryl, heteroaryl, hydroxyl, halogen, alkoxy, nitro, sulfhydryl, sulfonyl, amino (substituted and unsubstituted), acylamino, amido, alkylthio, carbonyl groups, such as esters, ketones, aldehydes, and carboxylic acids; thiolcarbonyl groups, sulfonate, sulfate, sulfinylamino, sulfamoyl, and sulfoxido.

"Polypeptide", "peptide", and "oligopeptide" encompasses organic compounds composed of amino acids, whether natural, synthetic or mixtures thereof, that are linked together chemically by peptide bonds. Peptides typically contain 3 or more amino acids, preferably more than 9 and less than 150, more preferably less than 100, and most preferably between 9 and 51 amino acids. The polypeptides can be "exogenous," or "heterologous," i.e. production of peptides within an organism or cell that are not native to that organism or cell, such as human polypeptide produced by a bacterial cell. Exogenous also refers to substances that are not native to the cells and are added to the cells, as compared to endogenous materials, which are produced by the cells. The peptide bond involves a single covalent link between the carboxyl group (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

The present disclosure relates to anti-fouling cross-linked polymer coatings and methods for making them and applying such coatings to a substrate. The present disclosure provides a method for coating a substrate with a nonfouling polymer. The substrate may be a surface on a house-hold item, and industrial item, or medical device. The medical device may be a wide variety of devices such as urinary catheters, neural prostheses, stenting devices, surgical instruments, scopes, probes, intraabdominal implants, dialysis machines, heart-lung bypass machines, tubing, vascular stents, dental implants, contact lens, cochlear implants, intravascular catheters, tubings (IV, arterial lines, central lines), ear tubes, plates, screws, pins, rods, active or passive middle ear implants, artificial spine discs, endotracheal or tracheotomy tubes, cerebrospinal fluid shunts, surgical drains, chest tubes and drains, endobronchial stents, urinary stents, bile stents, lacrimal stents, pacemakers, defibrillators, nerve stimulators, spinal cord stimulators, deep brain stimulators, implanted hernia meshes, implanted urogynecological meshes, intraocular lenses, cosmetic breast implants, cosmetic buttock implants, cosmetic chin implants, cosmetic cheek implants, birth control devices, drug delivery devices, machines or equipment (e.g. dialysis or heart lung bypass machines), and orthopedic implants. The household items may be a wide variety of items, such as restaurant utensils, baby spoons, and drinking cups that can resist bacterial adhesions with zwitterionic coatings. The anti-fouling polymer may resist scar formation and bacterial adhesion after implantation of a medical device, which can reduce complications following insertion including, but not limited to, device extrusion, device related infection, elevated impedances for neural prostheses, strictures, stent restenosis, and intraabdominal adhesions. The present technology reduces inflammation, infection, and fibrosis of electrode arrays that have been implanted into the cochlea.

In one embodiment, the present disclosure teaches a system. The system may comprise a cross-linked coating covalently bonded to a solid substrate. In one embodiment, the cross-linked coating may have a layer of zwitterionic polymer. In another embodiment, the cross-linked coating may have a layer of poly(ethylene) glycol. The cross-linked coating may be a hydrogel. The cross-linked coating may be configured to exhibit a micropattern and to resist biomolecule, tissue, or bacterial adhesion on the surface of a solid substrate. The zwitterionic polymer coating may be formed by photopolymerizing a zwitterionic monomer, such as carboxybetaine (meth)acrylate, carboxybetaine (meth)acrylamide, sulfobetaine (meth)acrylate, sulfobetaine (meth)acrylamide, phosphorylcholine (meth)acrylate, or phosphorylcholine (meth)acrylamide. Alternatively, the poly(ethylene)glycol polymer layer may comprise ethylene glycol monomer units.

In one embodiment, the present disclosure discloses a substrate, which may have a copolymer layer covalently bonded to the surface. The co-polymer may comprise repeating units. The repeating units may have the following structure:

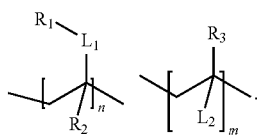

$R_1$ is a pendant group comprising a zwitterionic group; $R_2$, $R_3$ are each independently a hydrogen, substituted or unsubstituted alkyl, alkyloxy; $L_1$ is a linking group; n and m may be the same or different and are each an integer; and $L_2$ is a cross-linking group. In one embodiment, the co-polymer may comprise repeating units. The repeating units may have the following structures:

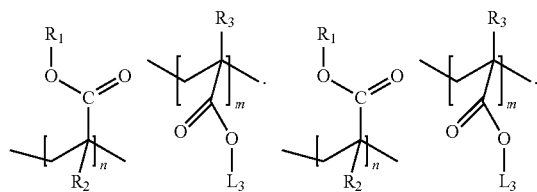

$R_1$, $R_2$, $R_3$, $L_1$, $L_2$, and n, m are defined above. $L_3$ is a linking group. In one embodiment, $L_3$ is $—(CH_2)_x—$, wherein x is an integer from about 1 to about 20.

In some embodiments, the co-polymer may comprise repeating units having the following structure:

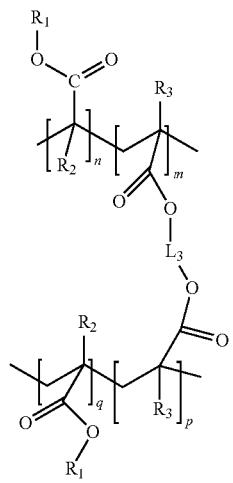

$R_1$, $R_2$, $R_3$, and n, m are defined above. $L_3$ is $(CH_2)_x—$, wherein x is an integer from about 1 to about 20, and p and q may be the same or different and are each an integer. In another embodiment, the co-polymer may comprise repeating units having the following structure:

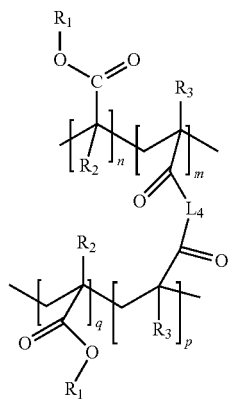

$R^1$, $R_2$, $R_3$, $L_1$, $L_2$, n, m, p, and q are defined above. $L_4$ is $—(O—CH_2—CH_2—)_y—O$, wherein y is an integer from about 1 to about 20.

In another embodiment, the substrate may be a synthetic polymeric substrate, which may be selected from the group consisting of polydimethylsiloxane (PDMS)), polypropylene, polyurethanes, polytetrafluoroethylene, polyethylene terephthalate, polyethylene, polyketones, poly(meth)acrylates, polyurethane, polylactides, polyesters, and polyether ether ketone (PEEK). In one embodiment, the polyethylene may be selected from the group consisting of ultra-high-molecular-weight polyethylene (UHMWPE) and cross-linked UHMWPE.

Zwitterions are molecules that carry formal positive and negative charges on non-adjacent atoms within the same molecule. Both natural and synthetic polymers, containing zwitterion functionality, have been shown to resist protein adhesion. In one embodiment, the zwitterionic monomer contains a phosphoryl choline moiety, a sulfobetaine moiety, a carboxybetaine moiety, derivatives thereof, or combinations thereof. Substrate surfaces treated with phosphoryl choline (PC), a natural zwitterionic molecule, not only exhibit reduced protein adsorption, but also exhibit increased blood compatibility, when compared to untreated substrate surfaces. Polymers created from phosphorylcholine are also considered biomimetic in addition to exhibiting the properties discussed above.

Sulfobetaine, closely resembles 2-aminoethanesulfonic acid, one of the most abundant, low molecular weight organic compounds found in animals. Sulfobetaine monomers are generally easier to synthesize than the corresponding carboxybetaine analogs.

Polycarboxybetaines are polymeric analogs of the naturally occurring zwitterion, glycine betaine. Similar to polyphosphorylcholines and polysulfobetaines, polycarboxybetaines are another class of zwitterionic, biomimetic polymers with exceptional resistance to biofouling. These polymers are particularly well suited for blood contacting applications due to anti-thrombogenic and anticoagulant properties unique to carboxybetaines. In addition to these properties, it is possible to design carboxybetaine monomers such that the resulting polymers contain reactive functional groups for immobilization of bioactive molecules.

Polysulfo- and polycarboxybetaines are not only biomimetic and highly resistant to bacterial adhesion, biofilm formation, and nonspecific protein adsorption from blood serum and plasma, they are also non-toxic, biocompatible and typically exhibit greater stability in complex media or in vivo when compared to both polyphosphorylcholine and poly(ethylene glycol), which may be degraded. The application of these materials and coatings can be further extended using biologically active agents, such as peptides. Other natural and synthetic zwitterionic chemistries can be used to design anti-fouling materials for the biomedical applications described herein.

Some examples of natural zwitterionic chemistries that could be used for anti-fouling materials include, but are not limited to, amino acids, peptides, natural small molecules including, but not limited to, N,N,N-trimethylglycine (glycine betaine), trimethylamine oxide (TMAO), dimethylsulfoniopropionate sarcosine, lysergic acid and psilocybin. Additional synthetic zwitterions that could be used to create anti-fouling materials, include, but are not limited to, aminocarboxyilc acids (carboxy betaines), amino-sulfonic acids (sulfo betaines), cocamidopropyl betaine, quinonoid based zwitterions, decaphenylferrocene, and non-natural amino acids. Natural and synthetic polymers also include mixed charged structures with both positive charged and negative charged moieties on the pendant groups, in the main chains, at the terminal groups, or on separate repeat units. In another embodiment, a polymeric composition is provided that includes a zwitterionic polymer covalently bound to a polymeric substrate, wherein the composition exhibits improved anti-fouling, antimicrobial, and/or anti-thrombotic activity as compared to a composition having linear zwitterionic polymer chains (brushes) bound to a substrate.

In some embodiments, the zwitterionic polymer may be a copolymer. Suitable comonomers include, but are not limited to, (meth)acrylates, (meth)acrylamides, vinyl compounds, and multifunctional molecules. Exemplary monomers are listed below:

Charged methacrylates or methacrylates with primary, secondary or tertiary amine groups include 3-sulfopropyl methacrylate potassium salt, (2-dimethylamino)ethyl methacrylate) methyl chloride quaternary salt, [2-(methacryloyloxy)ethyl]trimethyl-ammonium chloride, [3-(methacryloylamino)propyl]-trimethylammonium chloride), 2-aminoethyl methacrylate hydrochloride, 2-(diethylamino) ethyl methacrylate, 2-(dimethylamino)ethyl methacrylate, 2-(tert-butylamino)ethyl methacrylate, and 2-(tert-butylamino-ethyl methacrylate, for example.

Other monomers include, for example, ethylene glycol methyl ether methacrylate, di(ethylene glycol) methyl ether methacrylate, ethylene glycol phenyl ether methacrylate, 2-butoxyethyl methacrylate, 2-ethoxyethyl methacrylate, and ethylene glycol dicyclopentenyl ether methacrylate. Acrylamide and/or methacrylamide derivatives of the monomers listed above can also be used, as well as other monomers with unsaturated bonds. Multifunctional monomers, such di, tri, or tetra (meth)acrylates and (meth)acrylamides can be used to form highly cross-linked structures which can provide a more durable anti-fouling film.

The zwitterionic polymer may further comprise a crosslinker, which may be selected from the group consisting of ethylene glycol dimethacrylate (EGDMA), poly(ethylene glycol) di(meth)acrylate (PEGD(M)A) and derivatives, propylene glycol diacrylate, 1,3-butylene glycol dimethacrylate (BGDMA), 1,4-butane diol diacrylate (BDDA), 1,6-hexane diol diacrylate (HDDA), bisacrylamide, bisphenol A, ethoxylate diacrylate, N,N'-methylenebis(acrylamide), 1-carboxy-N-methyl-N-di(2-methacryloyloxy-ethyl) methanaminium inner salt, pentaerythritol tetraacrylate, trimethylolpropane triacrylate, he1,6-hexanediol dimethacrylate (HDDMA), neopentylglycol diacrylate (NPGDA) and trimethylolpropane triacrylate (TMPTA).

Without a crosslinker, the polymer will form linear chains from the surface which will not form covalent bonds between adjacent chains. By introducing a crosslinker, the system becomes more durable and a thicker polymer film can be achieved. The increase in thickness may allow more resistance to abrasion and wear. The currently used sulfobetaine methacrylate (SBMA) or carboxybetaine methacrylate (CBMA)-based polymer has shown superior performance at protein adsorption and cell adhesion resistance.

Figure 2:
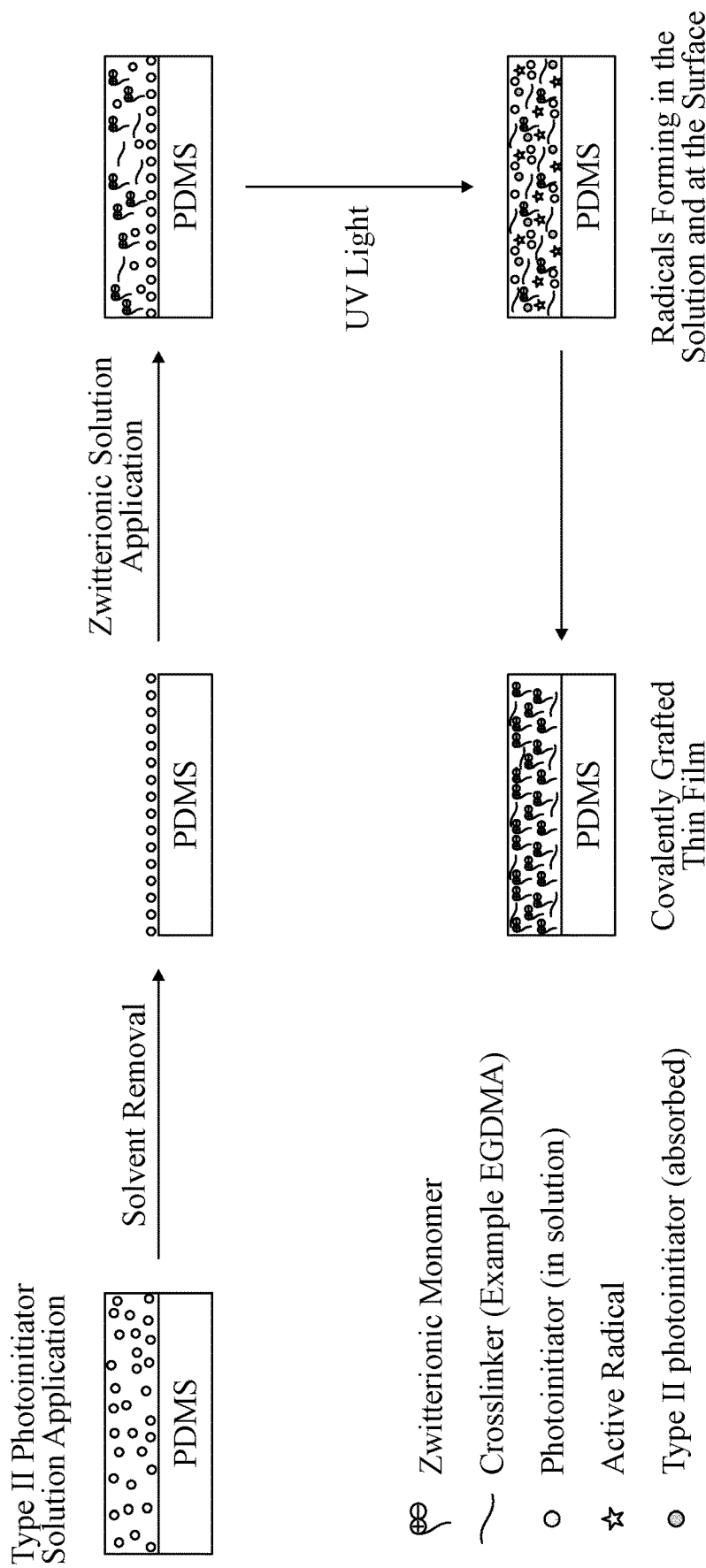
FIG. 2 is a schematic diagram illustrating one embodiment of a durable anti-fouling zwitterionic coating formed by a photo-chemical process, such as the process of FIG. 1, on the surface of a PDMS substrate.

The process scheme for coating polymer materials, such as those used in biomedical implants, is shown in FIGS. 1 and 2. A solution of type II (hydrogen abstraction) photoinitiator, such as benzophenone, is applied to the polymer surface. Alternatively, the hydrogen abstracting photoinitiator may first be adsorbed onto the polymer surface by submersing the polymer surface in a solution containing the photoinitiator. Type II photoinitiators that may be used in the process include camphorquinone and derivatives, benzophenone and derivatives, thioxanthone and derivatives, 6,7-dichloro-5,8-quinolinedione and derivatives, 1,4-naphthoquinone and derivatives, and naphthodioxinone-1,3-benzodioxole and derivatives. The polymer material is then dried and a solution of zwitterion-containing monomer and crosslinker, with or without additional photoinitiator, is applied to the surface. When one or more photoinitiators are added to the solution, polymerization can be initiated in the solution. Suitable photoinitiators that can be added to the solution include the type II photoinitiators previously mentioned, as well as a variety of type I photoinitiators. Representative examples of suitable type I photoinitiators include benzoin ethers, benzil ketals, acyl phosphine oxides, alpha-dialkyoxy acetophenone, alpha-hydroxyalkyl phenones, and alpha-amino alkyl phenones.

The polymer material is illuminated to initiate polymerization of the monomer system and graft the crosslinked zwitterionic network to the polymer surface. The source for the illumination can be any light source that can activate the photoinitiators. Typical light sources emit UV light and visible light. Upon illumination, the type II photoinitiator is excited to a highly reactive diradical state which may either abstract a hydrogen from the polymer, producing a radical at the surface, or react with a monomer, initiating polymerization in the solution. The radicals at the surface will also react with monomer double bonds or terminate with other growing radical polymer chains, effectively anchoring the coating to the polymer material surface. Upon illumination, the additional photoinitiator in the solution initiates additional polymerization in the solution, allowing crosslinking to occur both from the radicals generated at the material surface and in solution. After reaction at the surface and in solution, the growing polymer chains are incorporated covalently into the network of the zwitterionic coating. This covalent linkage provides a strong and durable adhesion between the crosslinked zwitterionic thin film and the polymeric substrate.

The type II photoinitiator is an important aspect of the process, without which the zwitterionic thin film may not adhere and may not be chemically bound to the surface. Because the zwitterionic coatings of the present technology are chemically bound to the substrate, they provide a distinct advantage over prior zwitterionic hydrogel coatings that are not covalently linked to the substrate and are therefore prone to delamination. Moreover, because polymerization of the zwitterionic monomers takes place in solution as well as at the surface of the substrate, the zwitterionic coatings of the present technology are crosslinked and are therefore more durable and thicker than prior zwitterionic brush coatings that are covalently grafted to the substrate using only surface initiating techniques.

Figure 3:
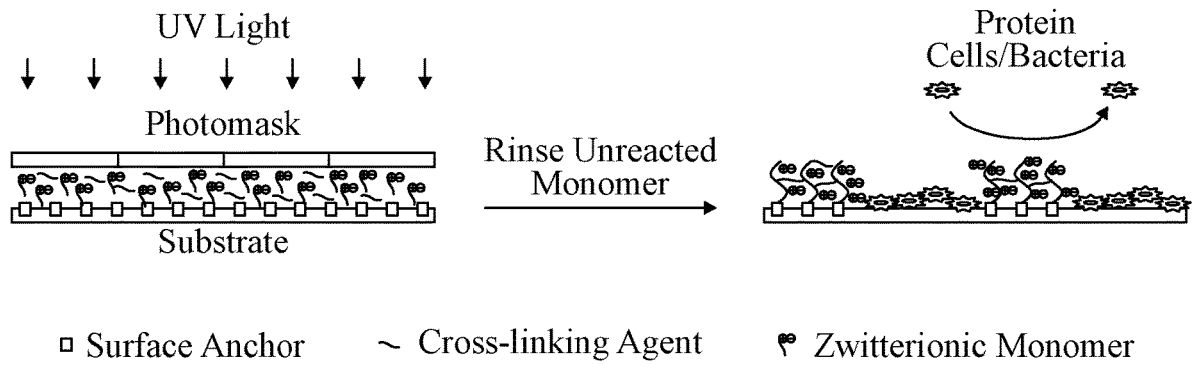
FIG. 3 is a schematic diagram illustrating one embodiment of a process using photo-masking to produce a patterned zwitterionic coating on the surface of a substrate.

Micropatterned zwitterionic coatings can be created using photomasking, a unique characteristic of the coating process, which has not been possible with previously described methods for zwitterionic coating. Photopolymerization during the coating process provides the ability to pattern zwitterionic thin films with great precision. Micropatterns composed of zwitterionic thin film patterns can be biologically relevant cues to multiple cell types. Patterned coatings may be created to direct cell or tissue growth in desirable configurations. Patterns of zwitterionic substrates may be created by using a photomask to have parallel bands of coating as illustrated in FIG. 3. These patterns provide strong directional guidance cues for Schwann cells and neurites from spiral ganglion neurons (SGNs) (see further below). These micropatterned zwitterionic coatings may become the basis for implant designs that guide spiral ganglion neurite extension towards cochlear implant electrode arrays.

An alternative approach to grafting zwitterionic polymers to PDMS or other silicone based chemistry surfaces could include using silane coupling agent chemistry. This process proceeds by exposing the PDMS sample to oxygen plasma. This step oxidizes alkyl groups on the surface of the PDMS to form hydroxyl functional groups. The sample may then be exposed to a solution of a silane coupling agent containing a methacrylate or other reactive group such as 3-(trimethoxysilyl)propyl methacrylate. Applying the silane coupling agent allows a covalent bond to form between hydroxyl groups on the surface and the silane coupling agent. A monomer can then be covalently grafted to the surface through photopolymerizing a zwitterionic solution in contact with the substrate. Polymerization of the zwitterionic solution was likely inhibited by oxygen imbedded in the PDMS substrate. Therefore, a crosslinked polymer was unable to form upon illumination to UV light.

Coating zwitterionic crosslinked films on the surface of PDMS or other polymer substrates could also be achieved through plasma treating. The PDMS is first exposed to plasma or UV/ozone to increase wetting and generate a more hydrophilic substrate for polymerization. The zwitterionic monomer could then be applied to the surface and illuminated to polymerize the sample. However, this method for coating does not form covalent bonds between the substrate and the crosslinked thin film. Consequently, the films may be more likely to delaminate and be much less durable than films generated using covalent grafting methods.

Customized zwitterionic monomers can be successfully grafted as thin films to a metallic substrate and other materials including glass, as well as PDMS polymer. The method for grafting zwitterionic coatings onto surfaces varies by material. A silane-based linker can be used to activate glass surfaces. Methacrylic acid can be used as an activating agent for metallic surfaces.

Coating titanium substrates with a high density of antifouling coatings may include surface modification to introduce functional groups on the titanium surface to covalently attach the coating. For example, hydroxyl groups can be created on the substrate surface using an oxidative piranha solution. These groups can then be used to covalently bind anchoring molecules presenting organic functional moieties. Alternatively a titanium oxide layer can be grown on the surface of titanium by heating in air at very high temperatures, e.g., 773-1073° K prior to piranha treatment.

Functional groups for anchoring undercoatings to titanium include, but are not limited to, silane, phosphonic acid, and catechol groups. For example, trimethoxy silanes and trichloro silanes can be introduced on to the surface of titanium substrates by exposing the substrate to a solution of the silane. The functional groups can be in the form of small molecules, oligomers, and/or polymers, including copolymers. Polymer brushes, combs, linear and branched copolymers, dendrimers, tethers and hydrogels can be formed by known synthetic means including, but not limited to, free radical polymerization, ionic polymerization, atom transfer radical polymerization (ATRP), nitroxide mediated polymerization (NMP), reversible addition-fragmentation polymerization (RAFT), ring opening metathesis polymerization (ROMP), telluride mediated polymerization (TERP) or acyclic diene metathesis polymerization (ADMET), and UV, thermal, or redox free radical polymerization. In a preferred embodiment, the polymer is formed using a photopolymerization process.

Materials containing, or composed of, these natural or synthetic zwitterions, can be applied to surfaces, particularly the surfaces of medical devices, in order to improve biocompatibility, reduce thrombogenesis (such as on the surface of stents or artificial valves), and reduce biofouling by proteins or bacteria present in solution. This is particularly applicable for surfaces where non-specific binding of proteins in solution could negatively impact the desired or necessary mechanics of a device.

The present disclosure further includes a process for coating a metallic substrate, which is selected from the group consisting of stainless steel, cobalt, chromium, tantalum, magnesium, titanium, nickel, nitinol (an alloy of nickel and titanium), platinum, iridium, and alloys thereof. These various surfaces are coated with a zwitterionic crosslinked thin film.

The metallic substrate may be a medical device. The medical device may be selected from the group consisting of a catheter, a vascular stent, a dental implant, cochlear implant, a surgical instrument, a scope, a probe, an intravascular catheter, a tubing (IV, arterial lines, central lines), an ear tube, a plate, a screw, a pin, a rod, an active or passive middle ear implant, an artificial spine disc, an endotracheal or tracheotomy tube, a cerebrospinal fluid shunt, a surgical drain, a chest tube and drain, an endobronchial stent, a urinary stent, a bile stent, a lacrimal stent, a pacemaker, a defibrillator, a nerve stimulator, a spinal cord stimulator, a deep brain stimulator, an implanted hernia mesh, an implanted urogynecological mesh, an intraocular lens, a cosmetic breast implant, a cosmetic buttock implant, a cosmetic chin implant, a cosmetic cheek implant, a birth control device, a drug delivery device, machines or equipment (e.g. dialysis or heart lung bypass machines), and an orthopedic implant.

The orthopedic implant may be selected from the group consisting of an implant for total knee replacement (TKR), total hip replacement (THR), total shoulder replacement (TSR), total elbow replacement (TER), total wrist replacement (TWR), total ankle replacement (TAR) and a component thereof.

A method has been developed to leverage the spatial precision of photopolymerization (use of light to drive and control the polymerization process) and provide durable coatings on PDMS and metal surfaces with micro-scale resolution. Zwitterionic polymeric thin film coatings of implant materials created with these novel photopolymerization techniques can significantly reduce protein and cell adhesion and tissue fibrosis.

One application of the present technology is in the area of cochlear implants.

Fibrotic tissue formation in the scala tympani is an expected consequence of cochlear implantation, and is detrimental to the user's hearing performance. When the implant is inserted, there is an initial inflammatory response, which then progresses to a fibrotic response that encapsulates the implant. The fibrotic capsule around the electrode array increases electrical impedance, necessitating the use of higher current levels and resulting in increased current spread. Spread of current decreases the number of perceptually separable channels of stimulation. The average cochlear implant user may be estimated to have only 6-8 distinct channels of stimulation though modern electrode arrays contain 12-22 electrode contacts. Despite increases in electrode number and improvements in signal processing, it has been difficult to improve sound perception for cochlear implant users beyond a crude and distorted representation. Fibrosis also likely contributes to delayed hearing loss following hearing preservation surgery. Histological examination of an early recipient of hearing preservation surgery who experienced late residual hearing loss showed a robust fibrotic reaction filling the scala tympani, which suggested that the fibrotic reaction was related to the late hearing loss. As hearing preservation cochlear implants implanted to less than the full depth of the cochlea become more widely implemented, it will become increasingly important to minimize the fibrotic reaction. Some degree of foreign body reaction has been identified in postmortem studies of almost all cochlear implant users. These cadaveric studies have further identified the foreign body reaction to the implant as a possible cause of implant extrusion or malpositioning and have found that new bone formation resulting from inflammation is correlated with poorer hearing outcomes. A small percentage of cochlear implant recipients also experience untoward reactions to the implant materials, such as silicone allergy, granulating labyrinthitis, ossification, and bony erosion. Unfortunately, these immune reactions continue to be difficult to predict and therefore continue to adversely affect a subset of cochlear implant recipients, sometimes resulting in the need for a revision surgery. Given that inflammation and resultant fibrosis is a root cause of many of these complications, intracochlear inflammation and the fibrotic response are important therapeutic targets.

Finally, the fibrotic response presents obstacles to strategies that seek to use the implant to deliver drugs or to attract neural growth towards the implant. Because of continued poor integration between cochlear implants and their target spiral ganglion nerve fibers, there has been interest not only in bringing the implant closer to the spiral ganglion but also in stimulating spiral ganglion fibers to extend closer to simulating electrodes. However, spiral ganglion neurites cannot traverse a fibrotic capsule. Improving integration between spiral ganglion nerve fibers and cochlear implant electrode arrays therefore depends on the ability to minimize the fibrotic reaction. Fibrosis therefore presents a barrier to the development of next-generation cochlear implants. A UV-based photopolymerization technique may allow for precisely controllable, durable coating for cochlear implant materials with zwitterionic thin films. Zwitterionic coatings were developed for in vitro work, using carboxybetaine methacrylate (CBMA) and sulfobetaine methacrylate (SBMA). Polyethylene glycol diacrylate (PEGDA) is used as a comparison. The PEGDA is a non-charged low-fouling biomaterial that resists cell adhesion to some extent. By contrast, PDMS is mechanically flexible, durable, and has excellent handling properties, but unfortunately generates a brisk fibrotic reaction. Despite this disadvantage, it remains the gold standard for cochlear implant housing material. A durable coating technique provided by the present technology is an attractive solution that takes advantage of the anti-fibrotic properties of zwitterionic hydrogels while preserving the handling characteristics of PDMS structures.

EXPERIMENTAL

Materials and Synthesis 2-(N,N'-dimethylamino)ethyl methacrylate (DMAEM), (3-propiolactone, triethyl amine, hydroquinone, [2-(Methacryloyloxy)ethyl]dimethyl-(3-sulfopropyl)ammonium hydroxide (SBMA), mouse anti-CD20 antibody, rabbit anti-S 10013 antibody, mouse anti-NF200 antibody, 3-(trimethoxysilyl)propyl methacrylate, paraformaldehyde, collagenase, dulbecco's modified eagle medium (DMEM), insulin, human fibrinogen, human anti-fibrinogen, and all organic solvents were purchased from Sigma Aldrich. Rabbit anti-vimentin and rabbit anti-glial fibrillary acidic protein (GFAP) antibodies were purchased from Abcam (Cambridge, MA). Hank's balanced salt solution (HBS), fetal bovine serum (FBS), poly-L-ornithine, trypsin-EDTA dissociation reagent, DAPI-containing mounting medium, were purchased from Gibco (Carlsbad, CA). Laminin was purchased from Labtek (Campbell, CA). Brain derived neurotrophic factor (BDNF) and neurotrophin-3 (NT-3) were purchased from R&D Systems (Minneapolis, MN).

2-Carboxy-N,N-dimethyl-N-(2'-(methacryloyloxy)ethyl) ethanaminium inner salt (carboxybetaine methacrylate, CBMA) was synthesized as follows. DMAEM was dissolved in acetone and cooled to 0° C. 3-propiolactone was dissolved in acetone and added to the DMAEM solution dropwise under inert atmosphere. The reaction was stirred overnight after which 10 mg of hydroquinone inhibitor was added and the solvent was removed. The residual oil was dissolved in methanol and trimethylamine was added to quench any side reactions. The solution was then precipitated into chilled diethyl ether and filtered to yield a white solid. The product was dried under vacuum and used without further purification. The NMR spectrum was recorded on a Bucker spectrometer (Avance 300). 1H NMR (D2O, 300 MHz), 6 6.06 (s, 1H, =CH), 6 5.68 (s, 1H, =CH), 6 4.55 (t, 2H, $OCH_3$), 6 3.70 (t, 2H, $NCH_2$), 6 3.59 (t, 2H, $NCH_2$), 6 3.10 (s, 6H, $NCH_3$), 6 2.64 (t, 2H $CH2COO$), 6 1.84 (s, 3H=$CCH_3$).

Zwitterion-Functionalized Glass Substrate Fabrication and Characterization

Due to the inherent spatial control afforded by photon-induced polymerization, zwitterionic polymers can be patterned by shuttering the light in regions where covalent grafting is not desirable. These patterns afford precise control over where fibrotic tissue forms allowing for fibrosis formation in desirable areas.

The general scheme for grafting zwitterionic polymers onto glass substrate surface is shown in FIG. 3.

Standard 2.54×7.62 cm glass microscope slides were functionalized with a 3-(trimethoxysilyl)propyl methacrylate (silane coupling agent) to allow covalent grafting of zwitterionic polymers onto glass surfaces. Zwitterionic polymers were grafted from glass surfaces represented schematically in FIG. 3. Aqueous monomer mixtures of zwitterion (CBMA or SBMA at 0.1, to 20 wt %) in phosphate buffered saline (PBS) containing 0.05 wt % 1-[4-(2-hydroxyethoxy)-phenyl]-2-hydroxy-2-methyl-1-propane-1-one (HEPK, photoinitiator) were pipetted onto the activated functionalized glass surfaces. The liquid was then dispersed evenly across the sample using a 2.54×2.54 cm glass-chrome Ronchi rule photomask for patterned samples or a cut glass slide of the same dimensions for uniform samples. Substrates were subsequently illuminated for 10 min at 16 mW/cm$^2$ measured at 365 nm wavelength using a mercury vapor arc lamp (Omnicure S 1500, Lumen Dynamics, Ontario, Canada). Samples were then copiously washed with distilled H$_2$O and dried using a nitrogen stream, then kept in a sealed container until use.

Contact angles were measured using the sessile drop method on a Rame-Hart Model 190 Goniometer. Five areas of each substrate were tested in triplicate, and the average contact angle was taken as the mean value of all fifteen measurements.

Protein Adsorption

Immunofluorescence was used to measure protein adsorption to substrates. The glass samples were first incubated in phosphate buffered saline (PBS) (room temperature) for 30 minutes prior to protein exposure. Human fibrinogen (1 mg/mL) was pipetted onto substrates and dispersed by placing a glass coverslip on the solution followed by an hour incubation at room temperature. The samples were then soaked in PBS for at least three hours with the PBS being changed every hour. After the rinsing step, the substrates were incubated in paraformaldehyde (4%) for 15 min at 2° C. The samples were then rinsed three times with PBS followed by a blocking buffer solution being applied to block the areas unoccupied by fibrinogen for 30 min at room temperature. An anti-fibrinogen antibody was applied to the samples overnight at 2° C. The substrates were then rinsed 3 times with PBS and a fluorescently tagged secondary antibody was applied for one hour at room temperature. The samples were washed three times with PBS and coverslips were applied before epifluorescent imaging. Digital epifluorescent images were captured on a Leica DMIRE2 microscope (Leica Microsystems, Bannockburn, IL) with Leica DFC350FX digital camera and Metamorph software (Molecular Devices, Silicon Valley, CA). Images were taken at each sample condition and gray-scale measurements were used to evaluate relative fluorescence intensity in Image J software (NIH, Bethesda, MD). All samples were made in triplicate and five representative images were taken for each condition.

Cell Culture and Immunofluorescence

Dissociated spiral ganglion (SG) culture from P4-7 perinatal rat cochleae was performed. Dissociated fibroblast cultures were obtained from P4-7 perinatal rat skin. The tissue was scraped to remove subcutaneous fat and digested in 0.125% trypsin with EDTA and 0.2% collagenase for one hour at 37° C. followed by gentle trituration. Astrocyte and Schwann cell cultures were prepared and maintained from P4-7 perinatal rat cerebral cortex and sciatic nerve, respectively. All cells were plated onto glass substrates without prior coating of protein.

SGN cultures were maintained in Dulbecco's Modified Eagle Medium (DMEM) supplemented with N$_2$ additives, 10% fetal bovine serum (FBS), NT-3 (50 ng/ml), and BDNF, (50 ng/ml). Fibroblast, Schwann cell, and astrocyte cultures were maintained in DMEM with 10% FBS. All cultures were fixed with 4% paraformaldehyde in PBS before immunostaining.

Spiral ganglia cultures were immunostained with anti-neurofilament 200 (NF200) antibodies to label neurons and their neurites. Astrocytes and Schwann cell cultures were immunostained with anti-GFAP or anti-S 100 antibodies, respectively. Fibroblast cultures were immunostained with anti-vimentin antibodies. Coverslips with DAPI-containing mounting medium were placed onto the stained cultures to label nuclei.

Quantification of Cell Density and Alignment to Micropatterns

Cell density was determined by counting the total number of nuclei of each cell type (identified by immunostaining as described above) from digital images of randomly selected 20× microscopic fields using the cell counting feature of MetaMorph software package. At least 10 fields were taken for each culture and each culture was placed before on at least 3 substrates per experiment. The experiments were repeated at least three times.

SGN total neurite length was determined from digital images captured using the scan slide feature in MetaMorph by measuring the longest process of randomly selected neurites from each condition using the measurement tool in Image J (NTH, Bethesda, MD). Neurite alignment was calculated. Briefly, alignment to the pattern was defined as a ratio of total length per aligned length. The ratio is represented as $[T_L/A_L]$, where $T_L$ is total neurite length and $A_L$ represents aligned length in the pattern direction. Aligned length ($A_L$) was determined by measuring the distance from the neuronal cell body to the neurite terminus in a straight line in the direction of the micropattern. The pattern direction was always set horizontally prior to measurements. The total length to aligned length ratio is referred to as the alignment ratio throughout the text. A ratio close to one represents a neurite that closely follows the pattern along its entire length. A wandering neurite, which does not strongly align to the pattern would be represented by a high alignment ratio. Schwann cell orientation to the pattern was determined as previously described by drawing the outline of the cell using Image J software and fitting an ellipse to the cell outline. The angle made between the major axis of the ellipse and the pattern (θ) was measured in Image J as Schwann cell alignment.

Statistics

Statistical analysis was conducted using Graphpad Prism 7.01 software. To compare cell density between uncoated, CBMA-coated, and SBMA-coated and between striped groups on patterned substrates, a one-way ANOVA with post hoc Tukey test was used. A two-tailed t-test was used to compare cell density between coated and uncoated regions on striped substrates. Analysis of alignment of Schwann cells and SGN neurites was conducted using a one-way ANOVA by a post hoc Kuskal-Wallis analysis of variance on ranks and a Dunn's test.

Results and Discussion

Zwitterion-Functionalized Substrate Fabrication and Characterization
Glass Used as a Substrate
Surface properties are a key component when engineering low fouling materials because the surface comes into direct contact with host fluid, blood protein, and other immunogenic factors. These biomolecules and their nonspecific adsorption to implant surfaces play an integral role in fibrous tissue formation. A common approach to achieve nonfouling properties involves introducing functional groups onto the surface, which then act as anchors for polymer growth.

Glass was used as a proof of concept substrate because it can be easily modified with a variety of functional groups using silane coupling chemistry. The system uses photopolymerization as a simple method to covalently graft and pattern zwitterionic polymers on the surface. The systems were used to investigate adhesion of cell types relevant to neural regeneration (Schwann cells, and spiral ganglion neurons), which have not been previously studied on zwitterionic polymer thin films, in addition to fibroblasts, critical in fibrotic tissue formation. To fabricate these substrates, glass samples were first exposed to oxygen plasma to generate hydroxyl surface groups followed by reaction with a silane-containing coupling agent incorporating a reactive methacrylate group. Zwitterionic methacrylates were then covalently attached to glass surface methacrylates by illuminating a monomer- and photoinitiator-containing solution in contact with the substrate. UV-light was used to induce the polymerization reaction and covalently build a grafted zwitterionic polymer from the substrate (FIG. 3).

During UV-illumination, radicals in the solution are generated from photo initiating molecules absorbing light that dissociate into initiating species. These initiating radicals then react with methacrylates on the surface and in the solution to generate a propagating species that builds the zwitterionic polymer from the surface of the glass slide. For experiments, SBMA and CBMA (FIG. 4A) were used as zwitterionic monomers to alter the surface properties of functionalized glass substrates. The concentration of zwitterionic monomer in solution was varied between 0.1 wt % and 20 wt % to change surface coverage and probe the physicochemical properties of the antifouling polymer-grafted surface.

Surface grafting of a polymer or other molecule is accompanied by a corresponding change in surface properties including surface energy that can be evaluated using water contact angle measurements. Higher contact angles indicate a more hydrophobic surface as water avoids interaction with the surface. Conversely, low contact angles indicate hydrophilic surfaces as water spreads to maximize interactions with the substrate. The silanized glass was relatively hydrophobic with a contact angle of over 57 degrees as would be expected given the nonpolar nature of the coupling agent used to functionalize the glass substrates. Conversely, zwitterionic polymers are hydrophilic, due to the presence of charged atoms along the polymer side chains and are expected to decrease contact angles.

Figure 4A:
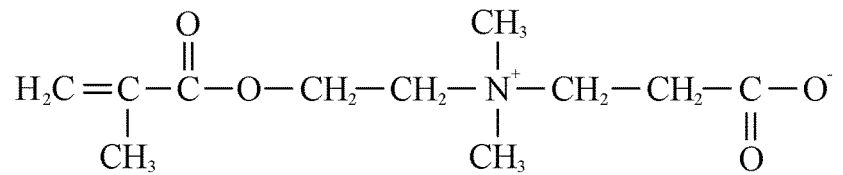
FIG. 4A illustrates carboxybetaine methacrylate (CBMA), sulfobetaine methacrylate (SBMA) and polyethylene glycol diacrylate (PEGDA) structures.
Figure 4A:
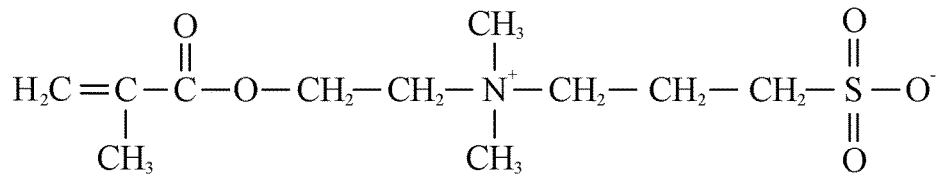
Figure 4A:
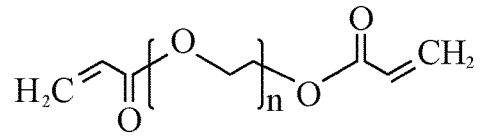
Figure 4B:
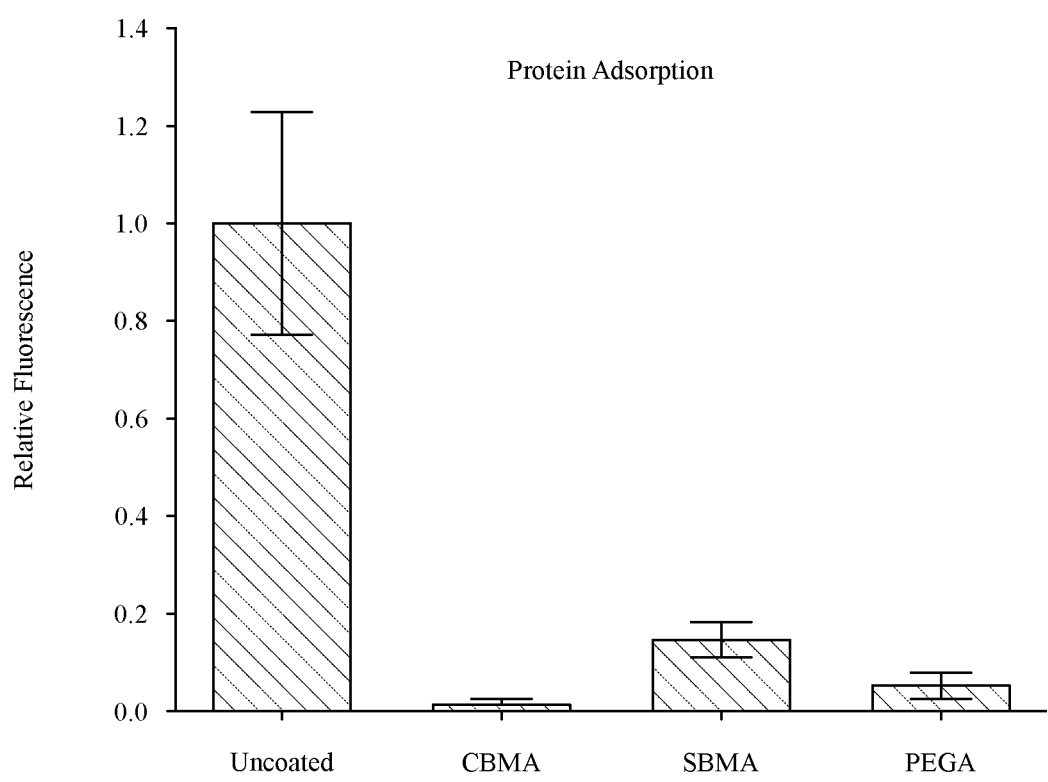
FIG. 4B is a graphical representation of protein adsorption on glass surfaces with zwitterionic CBMA and SBMA coatings and a polyethylene glycol acrylate (PEGA) coating, as indicated by fluorescence intensity relative to an uncoated glass control surface.

Glass slides coated with zwitterionic thin films may resist fibrinogen adsorption. To evaluate the ability of zwitterionic thin films to resist protein adsorption, the levels of fibrinogen adsorption to coated and uncoated glass slides were studied. FIG. 4A shows the chemical structures of the monomers of carboxybetaine methacrylate (CBMA), sulfobetaine methacrylate (SBMA) and polyethylene glycol acrylate (PEGA). Slides were incubated in fibrinogen solution (1 mg/ml) for 1 hour, rinsed 3 times with phosphate buffered saline (PBS) and fixed with 4% paraformaldehyde. Slides were immunostained with anti-fibrinogen antibodies then a fluorescently tagged secondary antibody. The slides were imaged with a DMIREII Leica epifluorescence microscope running Metamorph software. After subtracting background fluorescence, fluorescence intensity relative to the uncoated control glass was then calculated. FIG. 4B illustrates relative fluorescence intensity calculated relative to uncoated glass control with error bars representing standard derivation (n=3 slides with 10 images per slide). Thin film coatings of CBMA, SBMA, and PEGA significantly reduced fibrinogen adsorption compared to uncoated glass, with CBMA showing the strongest effect (FIG. 4B).

Schwann and Fibroblast Cell Adhesion

Figure 5A:
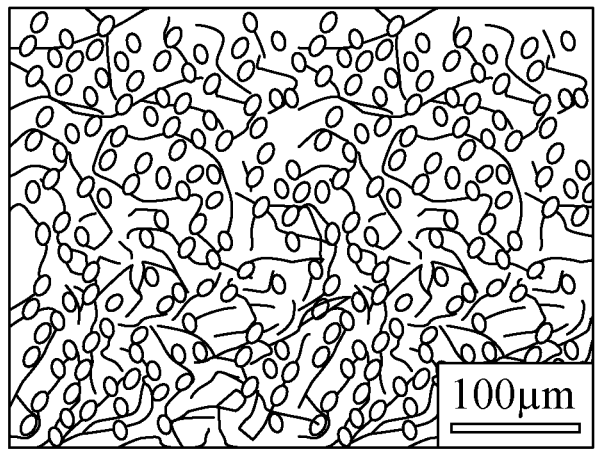
FIG. 5A illustrates Schwann cell density after 48 hours of culture on an uncoated glass.
Figure 5B:
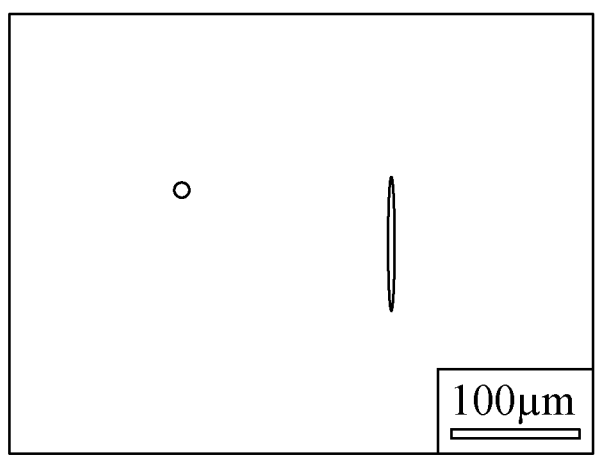
FIG. 5B illustrates Schwann cell density after 48 hours of culture on a CBMA coated glass.
Figure 5C:
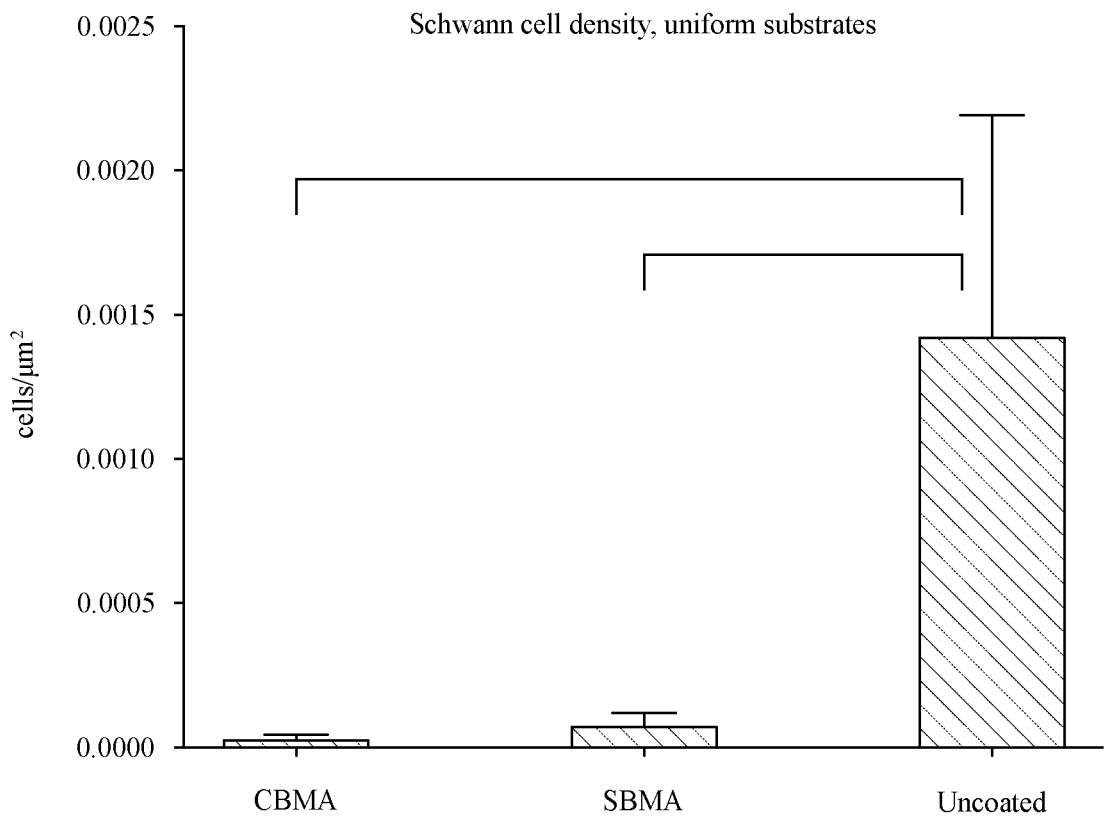
FIG. 5C illustrates nucleus counts showing that both CBMA coating and SBMA coating significantly reduce Schwann cell adhesion.

Schwann cells are the principal myelinating cell type of the peripheral nervous system and function to support the growth and development of neurons. It is therefore important to understand how these cells interact with zwitterion-coated substrates especially for potential neural prosthesis applications. Schwann cells show decreased adhesion to SBMA and CBMA coated glass substrates compared to uncoated glass. Schwann cells cultured on uncoated and CBMA coated glass surfaces are shown in FIGS. 5A and 5B respectively. Cell nucleus counts for Schwann cells are shown in 5C. A significant reduction in nucleus counts was seen on SBMA and CBMA coated glass compared to uncoated glass. These data suggest that zwitterionic thin films effectively prevent Schwann cell adhesion.

Figure 5D:
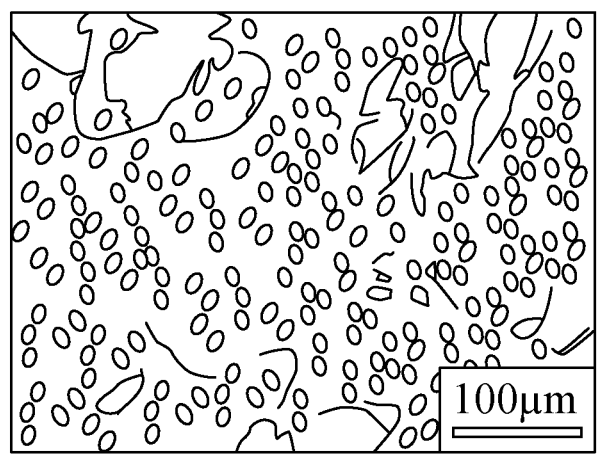
FIG. 5D illustrates fibroblasts on uncoated glass.
Figure 5E:
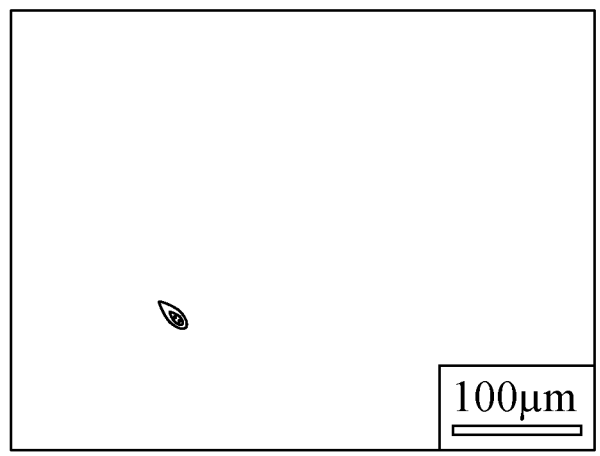
FIG. 5E illustrates fibroblasts on CBMA coated glass.
Figure 5F:
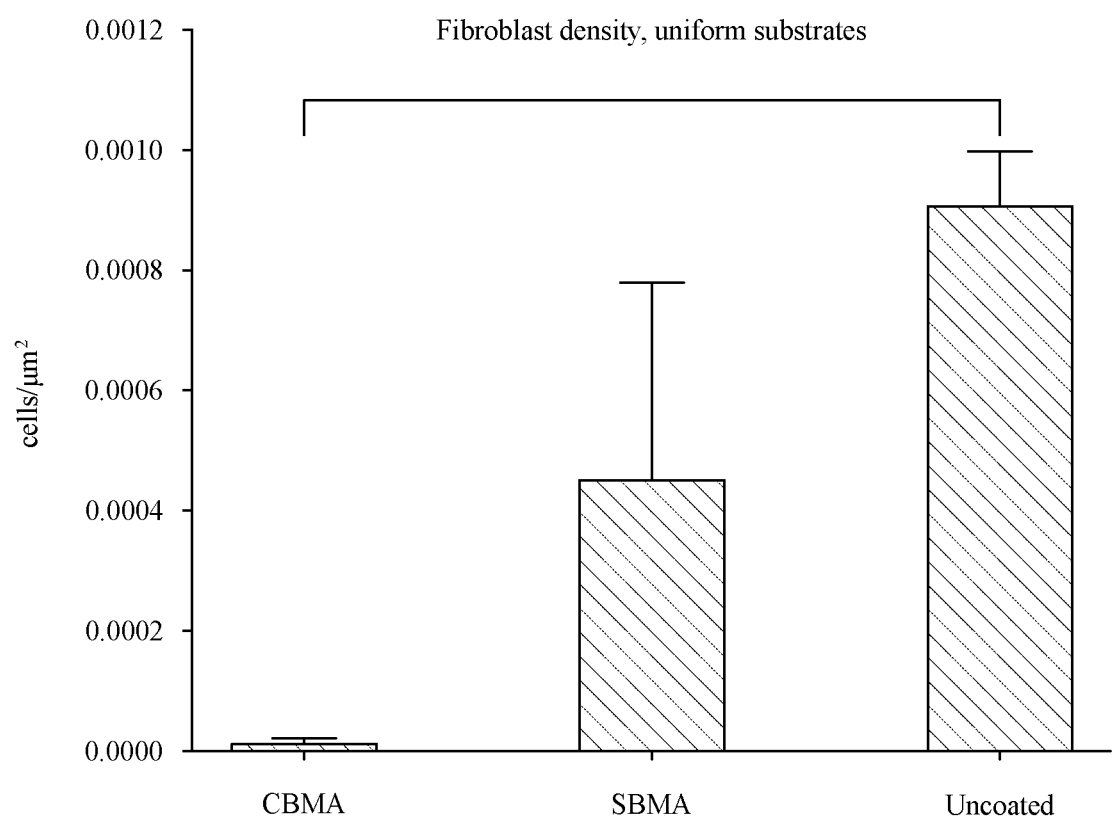
FIG. 5F illustrates nucleus density showing that CBMA and SBMA coatings significantly reduce fibroblast adhesion.

Fibroblasts are the primary cell type that contributes to fibrosis on the surface of implanted devices. Therefore, determining the effectiveness of these zwitterion-coated substrates in preventing adhesion of fibroblasts could serve as an effective in vitro measure of the ability of these materials to resist fibrosis. Thus, fibroblasts were cultured on SBMA, CBMA coated substrates and compared to a glass control. The morphology of fibroblasts cultured on zwitterion coated substrates was markedly different from uncoated glass (FIG. 5E). On uncoated glass, fibroblasts showed a characteristic elongated multipolar shape, while they showed fewer cytoplasmic extensions and exhibited a round morphology on zwitterion-coated substrates (FIG. 5D). Further, noticeably fewer cells adhered to CBMA-coated substrates compared to SBMA-coated substrates. Random images were analyzed and cell nuclei counts were performed to determine cell density. Analysis of fibroblast cell density on uniform substrates reveals a statistically significant reduction in adhered cells to SBMA-coated surfaces with less than half of the cell density when compared to uncoated glass (FIG. 5F). Very few fibroblasts adhered on CBMA-coated surfaces with less than one percent of the cell density as compared to the uncoated glass.

Schwann cell and fibroblasts were then cultured onto SBMA and CBMA patterned surfaces with a 100 μm periodicity pattern.

Figure 6A:
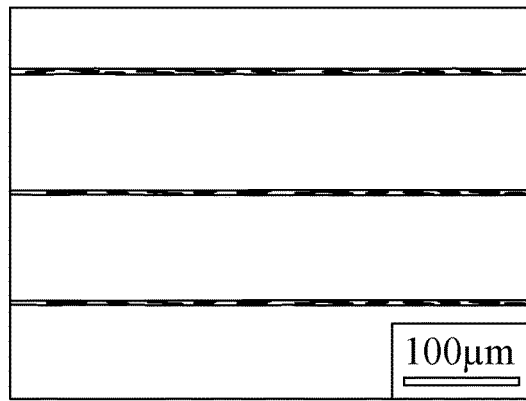
FIG. 6A illustrates photopatterned zwitterionic coatings on glass substrates showing resistance to Schwann cell adhesion in the coated regions.
Figure 6B:
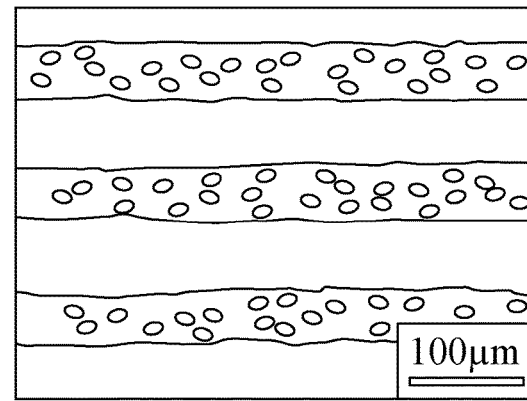
FIG. 6B illustrates photopatterned zwitterionic coatings on glass substrates showing resistance to fibroblast adhesion in the coated regions after 48 hours in culture.
Figure 6C:
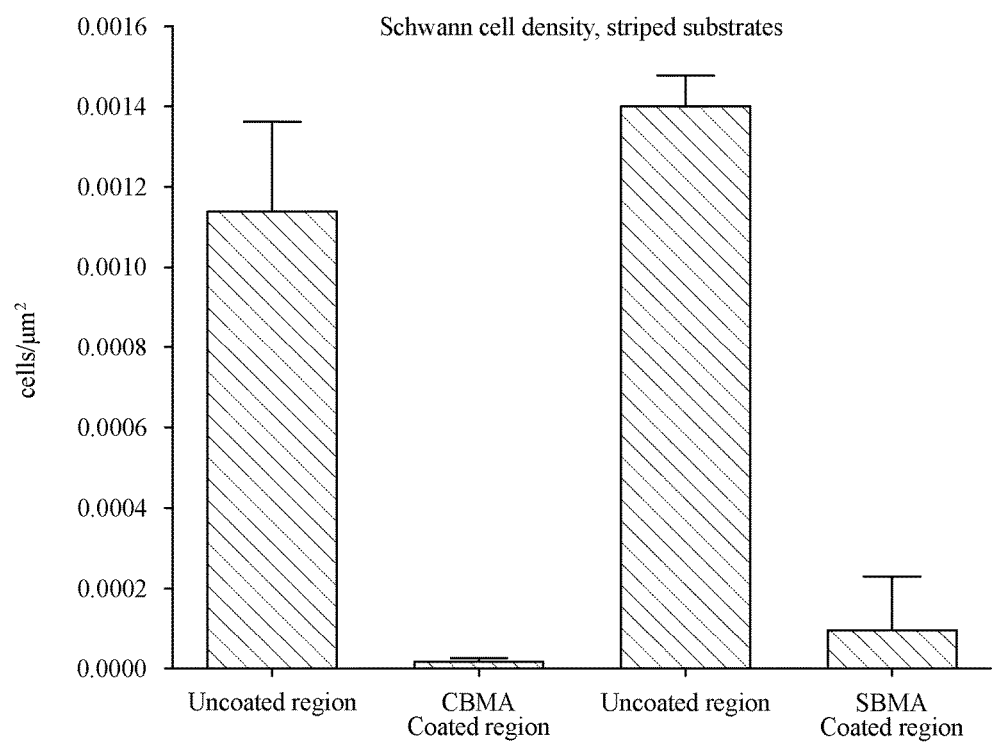
FIG. 6C illustrates nucleus density on photopatterned glass substrates revealing a statistically significant reduction in Schwann cell adhesion in the region with a CBMA coating on a first substrate compared to the uncoated region on that first substrate, and a statistically significant reduction in Schwann cell adhesion in the region with a SBMA coating on a second substrate compared to the uncoated region on that second substrate.

Analysis of cell density on these patterned substrates showed a distinct preference for cell adhesion to uncoated glass compared to adjacent SBMA- or CBMA-coated stripes. FIG. 6A shows Schwann cells cultured on a CBMA patterned substrate. The Schwann cells are observed elongating along the length of the uncoated regions avoiding interactions with the adjacent CBMA coated bands. Analysis of Schwann cell density on SBMA and CBMA patterned substrates is shown in FIG. 6C. The CBMA and SBMA coated regions were shown to significantly reduce the Schwann cell adhesion compared to the adjacent uncoated bands.

Primary fibroblasts also showed a similar outcome when cultured on SBMA and CBMA striped substrates. FIG. 6B depicts fibroblasts growing exclusively on uncoated regions of a glass substrate patterned with 100 μm CBMA stripes. The fibroblasts not only stayed within uncoated stripes, but also extended their cytoplasmic processes to the border of the uncoated areas, almost never extending into coated areas (FIG. 6B).

Figure 6D:
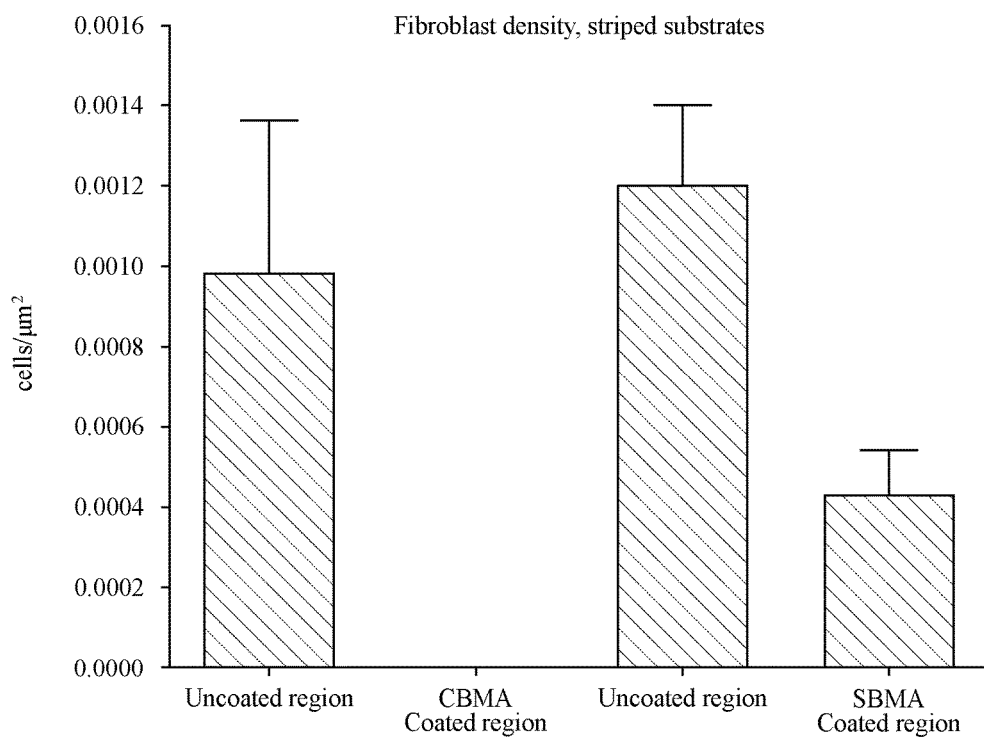
FIG. 6D illustrates fibroblast cell density on photopatterned glass substrates revealing a statistically significant reduction in fibroblast adhesion in the region with a CBMA coating on a first substrate compared to the uncoated region on that first substrate, and a statistically significant reduction in fibroblast adhesion in the region with a SBMA coating on a second substrate compared to the uncoated region on that second substrate.

Quantification of fibroblasts grown on zwitterion patterned glass showed a statistically significant difference in cell density between coated and adjacent uncoated regions for SBMA and CBMA patterned substrates (FIG. 6D). Remarkably, zero fibroblasts were observed adhered to CBMA stripes while uncoated regions had a similar cell density to the uncoated regions of the SBMA-striped substrates. A significant difference was found in cell density between SBMA and CBMA stripes, further corroborating the effectiveness of CBMA over SBMA films in preventing fibroblast cell adhesion.

SGN Neurite Alignment to Zwitterionic Micropatterns

Figure 7A:
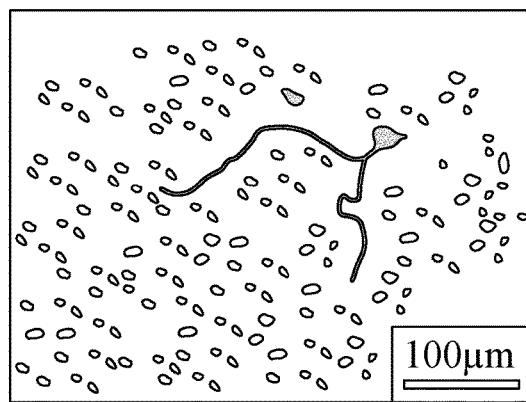
FIG. 7A illustrates primary spiral ganglion cells cultured on uncoated glass.
Figure 7B:
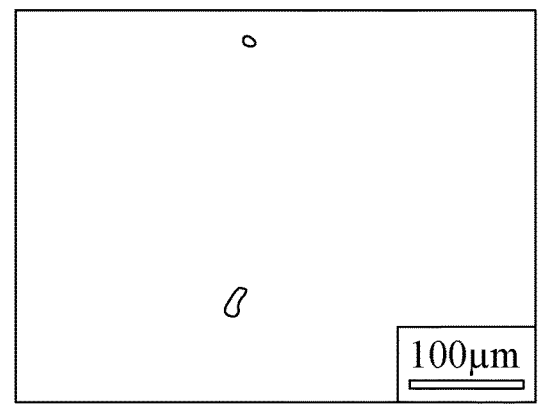
FIG. 7B illustrates primary spiral ganglion neuron cells cultured on glass with an unpatterned CBMA coating.

Spiral ganglion neurons (SGNs) are the afferent neurons of the inner ear that innervate hair cells in the organ of Corti in the hearing ear. In deafened cochleae with a cochlear implant, SGNs are the target neural elements that are stimulated by cochlear implant electrodes. However, a number of factors (including scar tissue formation and distance between SGNs and cochlear implant electrodes) compromise the fidelity with which cochlear implants mimic native hearing. Patterned coatings may affect the alignment of SGN neurites and may form the basis for an implant with an improved interface with its target neural elements. Accordingly, neonatal rat spiral ganglia were plated directly onto both plain glass and zwitterion-patterned substrates. Micropatterned zwitterionic coatings could direct spiral ganglion neurite extension. Primary mixed spiral ganglion cell cultures were prepared from p4-7 rats as previously described and were plated onto glass slides with or without zwitterionic thin film coatings. After 48 hours, they were fixed and immunostained using anti-NF-200 antibody to identify spiral ganglion neurons and visualize neurites extending from the soma.SGN neurite growth on uncoated substrates (FIG. 7A) reveals random growth Unsurprisingly, when coated with SBMA or CBMA, SGN neurite density is greatly decreased as observed in FIG. 7B (CBMA depicted). Alignment of SGN neurites along CBMA-coated substrates shows a preference to grow on the uncoated regions (FIG. 7C). Alignment of SGN neurites to CBMA-coated patterns revealed neurite segments that extend along the middle of the uncoated bands and generally do not deviate from parallel patterns, in contrast to the occasional extension of a neurite across an SBMA-coated stripe.

Importantly, as SGNs extended neurites over micropatterned substrates, these neurites remained on the uncoated regions almost exclusively, resulting in strong orientation parallel to the striped pattern (FIG. 7C). Micropatterned zwitterionic coatings appear to strongly direct both Schwann cell alignment (FIG. 6A) and neurite growth (FIG. 7C). These data demonstrate the ability of the photopolymerization technique to precisely control deposition of zwitterionic thin film coatings. Such spatial control can be leveraged to direct specific cellular responses such as directional neurite or Schwann cell growth.

Cell Alignment to Zwitterionic Patterns

Figure 8C:
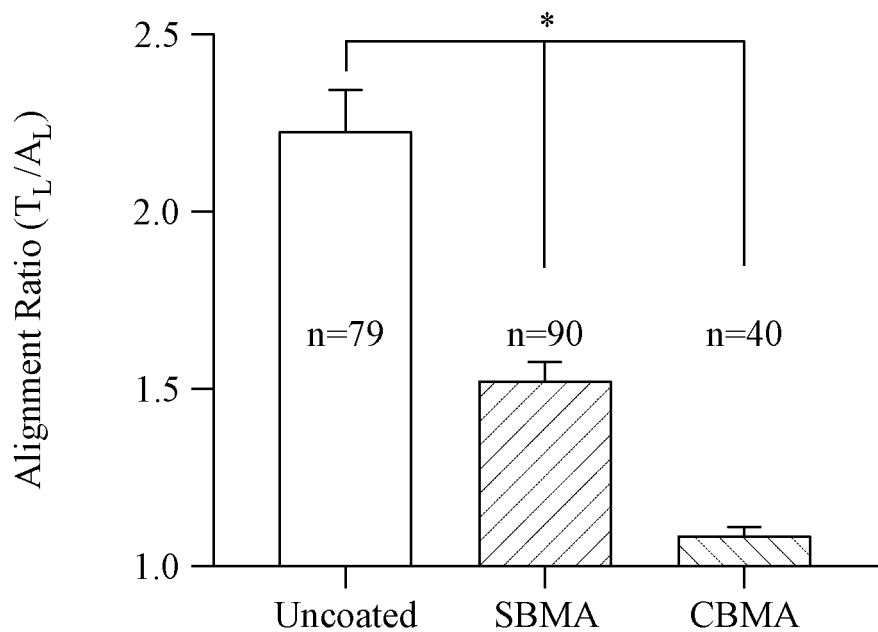
FIG. 8C is a graphical representation showing the alignment ratio of spiral ganglion cells on plain uncoated glass, glass with a patterned SBMA coating, and glass with a patterned CBMA coating.

FIG. 8A shows a schematic measurement of neurite length, and the measurement of cell body to nerve terminus parallel to the pattern. FIG. 8B shows Schwann cell alignment determined by measuring the angle ($\theta$) of an ellipse fitted to the major axis of the cell relative to the pattern. Preliminary studies suggest that micropatterned the zwitterionic coatings strongly influence SGN neurite extension. In substrates where zwitterionic coating is patterned in stripes, neurites may align parallel to these stripes Schwann cells grown on uncoated glass substrates were randomly oriented with a mean angle of about 42 degrees (FIG. 8C). By comparison, SBMA-patterned substrates were aligned parallel to the stripes with an average angle of less than 6 degrees. Cells on CBMA substrates were even more closely aligned to the stripes with an average angle of just under 2 degrees. The alignment of the Schwann cells appeared to occur because the cells were repelled by the zwitterionic stripes. Schwann cells cultured on substrates with CBMA stripes almost never crossed into the zwitterionic regions forming distinct boarders between coated and uncoated areas.

Figure 8D:
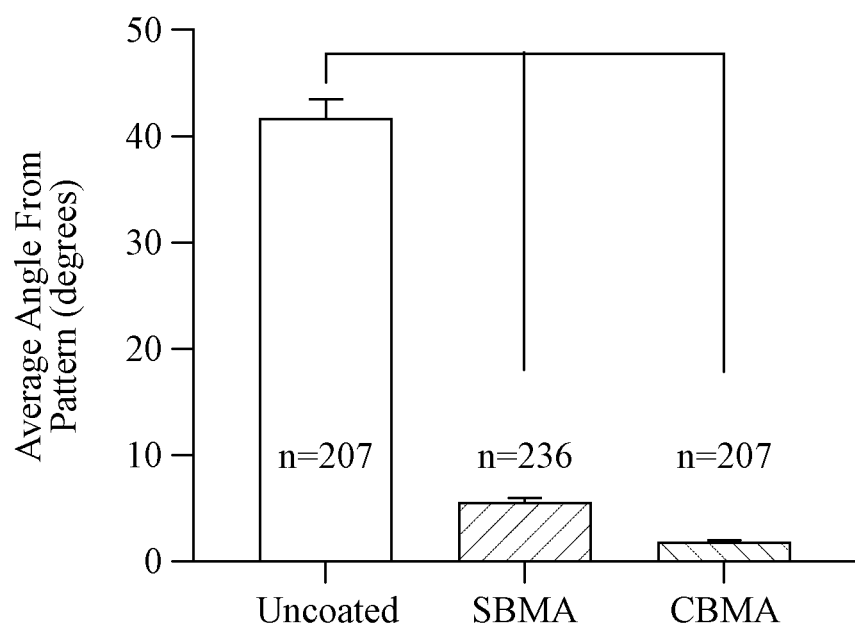
FIG. 8D is a graphical representation showing average angle angle of orientation of Schwann cells on plain uncoated glass, glass with a patterned SBMA coating, and glass with a patterned CBMA coating relative to the pattern.

To quantify alignment of SGN neurites to the zwitterionic patterns, alignment ratios were calculated by dividing the total length along the path of the neurite by the aligned length ($T_L/A_L$) as measured using the trace tool in Image J where the aligned length ($A_L$) is the distance the neurite travels in the direction of the pattern. Therefore, an alignment of 1 indicates perfect alignment while larger values indicate greater deviations from the parallel path. As shown in FIG. 8D, SGN neurites evaluated on glass showed an alignment ratio of over 2.2, whereas neurites on SBMA-striped substrates showed an alignment ratio of approximately 1.5. Neurites on CBMA-striped substrates exhibited an amazingly low alignment ratio of 1.09. A statistical difference was found between all samples groups. CBMA samples direct alignment almost perfectly to the pattern, while SBMA stripes also showed a noticeable effect on neurite alignment. These results suggest that zwitterionic coatings may be used to not only reduce undesirable cell adhesion, but also could be used to guide neurite extension toward a target such as a neural prosthetic device. Similarly, photopatterning could allow for directed fibroblast or glial adhesion and growth in circumstances where patterning of these cells is desirable.

Protein adsorption, cell adhesion, and cell alignment may be compared among the different surfaces using a one-way ANOVA with post-hoc Dunn's method. With neurite alignment, which tends to not be normally distributed, one-way ANOVA on ranks may be used followed by Kruskal-Wallis post hoc analysis as previously described. Based on preliminary and prior studies, an analysis of approximately 100 neurites and Schwann cells should reliably yield statistically meaningful results.

Fibrinogen, albumin, and fibronectin may adsorb significantly less to coated PDMS and platinum-iridium than they do to uncoated substrates. There may be significantly less cell adhesion on zwitterionic-coated PDMS substrates than on untreated substrates. Accordingly, zwitterionic thin film coatings may represent strong candidates for incorporation into cochlear implant technology. Schwann cell and spiral ganglion neurites may strongly align to micropatterns on PDMS and platinum-iridium substrates. Zwitterionic patterns could be incorporated into three-dimensional scaffolds, and could ultimately inform next-generation cochlear implant design in improving the neural to prosthesis interface by guiding spiral ganglion neurites and/or Schwann cells while preventing fibrosis.

Similar to the above-mentioned experiments, uncoated, unpatterned SBMA- and CBMA-coated, and 100 µm periodicity (both SBMA and CBMA) glass substrates were examined for Schwann cell growth. Cell morphology on uncoated substrates was visibly different for SBMA- and CBMA-coated surfaces with cells spreading and interacting with adjacent cells. Conversely, Schwann cells grown on SBMA-functionalized substrates appeared less dense and showed a rounded morphology. Few cells were visible in CBMA-coated substrates with very little spreading. Quantification of cell density on uniformly SBMA-coated substrates revealed more than a 40 fold decrease in Schwann cell density compared to uncoated substrates, a larger effect than seen for fibroblasts or astrocytes. Similar to the findings with fibroblasts and astrocytes, CBMA-coated surfaces experienced more than double the reduction in cell density with over 80 times decrease in Schwann cell density on CBMA coated substrates compared to uncoated controls.

Analysis of Schwann cell growth on patterned substrates showed similar results with a repulsion of cell adhesion on coated regions as opposed to uncoated areas. Schwann cells grown on glass substrates, with both SBMA and CBMA stripes, elongated parallel to the zwitterionic bands. Quantification of cell density on SBMA stripes showed a relatively modest 13 fold reduction in cell density on coated bands as opposed to uncoated bands, significantly less than for uniformly-coated substrates but still much greater than for most other cells. Conversely, on CBMA-striped substrates, Schwan cell density decreased over 150 fold over coated regions compared to uncoated regions. This repulsion was even greater than that observed for uniformly-coated surfaces. While the CBMA-coated substrates yielded a larger decrease in cell density, both SBMA and CBMA polymer brushes showed a significant reduction when compared with the adjacent uncoated band ($p<0.001$, t-test).

Schwann cells provide trophic support to neurons, myelinate axons and guide axon regeneration when peripheral nerves are disrupted. Regenerating neural cells have been shown to closely align with Schwann cells in culture, suggesting that the ability of substrates to cause Schwann cell alignment might allow for control of axonal pathfinding.

PDMS Polymer as a Substrate

Zwitterionic coatings of materials commonly used in cochlear implants (PDMS, platinum-iridium) may be tested in vitro for their ability to resist protein and cell adhesion by comparing protein adhesion and cell adhesion on coated and uncoated substrates.

Adsorption of protein is an initial step required for the formation a provisional matrix on the surface of an implanted foreign body, which then facilitates adhesion of immune cells and fibroblasts. Therefore, if protein adsorption is prevented or reduced, the immune response and fibrotic tissue formation would be thwarted. Quantifying protein adsorption level is therefore useful to predicting the capacity of zwitterionic thin films resist the foreign body reaction. Thin sheets of sterile surgical grade PDMS and glass slides sputter coated with platinum-iridium may be coated with CBMA or SBMA. Control slides may lack the polymeric thin film coating. Protein adsorption to these surfaces was tested using several structurally distinct proteins known to adsorb onto implanted substrates and to participate in the early foreign body response. These include albumin, fibrinogen, and fibronectin. Protein adhesion may be quantified by immunofluorescence as described above for glass substrates (FIG. 4C).

Cell adhesion assays may be done using a variety of rat-derived primary cell types, including fibroblasts, Schwann cells, and SGNs as above. Cell adhesion was quantified by scoring the number of cells that adhere to the substrates. Primary cultures of fibroblasts, Schwann cells, and SGNs may be prepared. For fibroblast and Schwann cell cultures, skin and sciatic nerve respectively may be isolated from p4-7 rats and maintained as a primary cell line prior to plating onto substrates. For spiral ganglion cultures, the spiral ganglia may be isolated from p4-7 rats, dissociated and plated directly onto the substrates, as neurons typically do not survive passaging once plated. Cultures were fixed with 4% paraformaldehyde after 6, 24, or 48 hours followed by immunostaining for cell type specific markers (vimentin for fibroblasts, S100 for Schwann cells, and NF200 for neurons). Cells fixed at 6 hours are more likely to reflect differences in initial adhesion, whereas cells fixed at 48 hours may reflect differences in cell survival in addition to cell adhesion.

Figure 9:
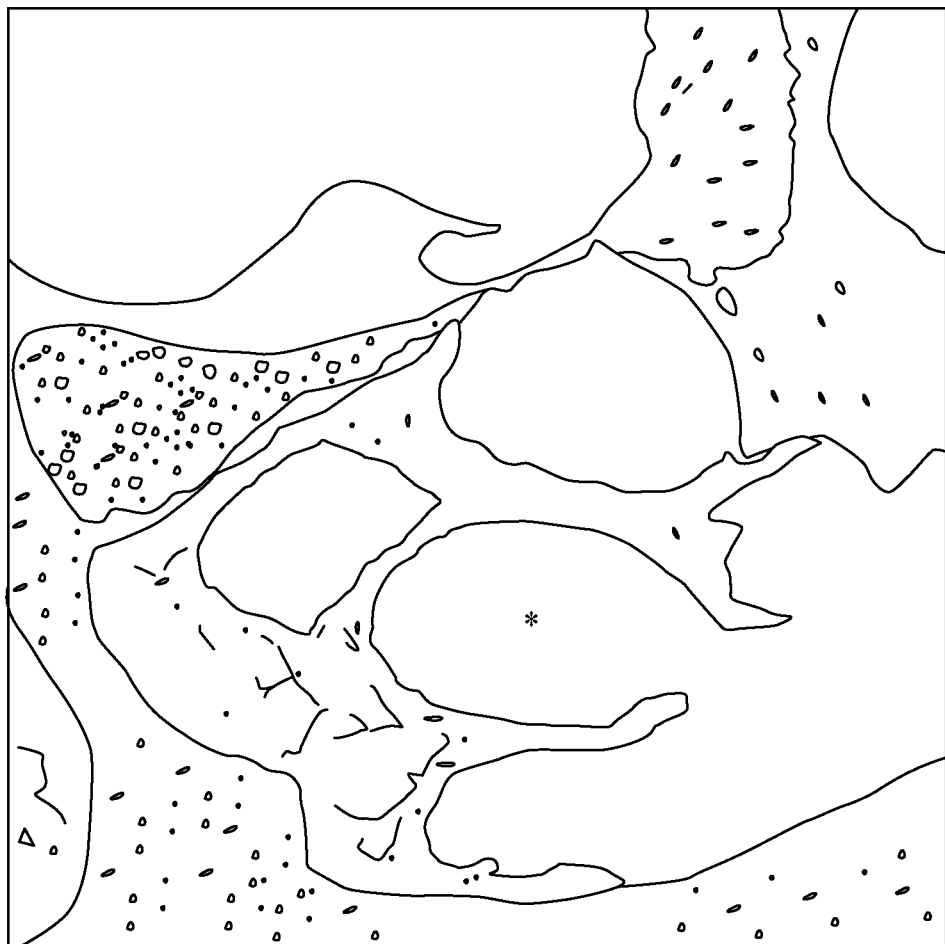
FIG. 9 is a cross-sectional depiction of a basal turn of the mouse scala tympani following PDMS implantation revealing significant scar tissue formation at 22 weeks.
Figure 10C:
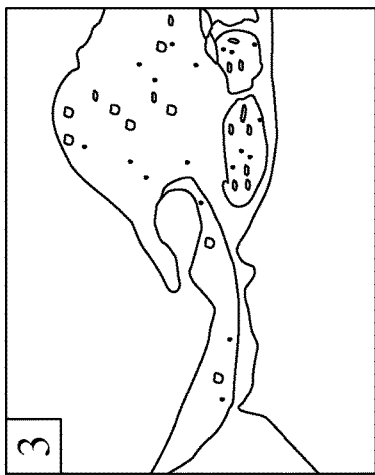
FIGS. 10A-10E illustrate an organ of Corti ordinal grading system with representative histologic sections at 20× magnification.
Figure 10B:
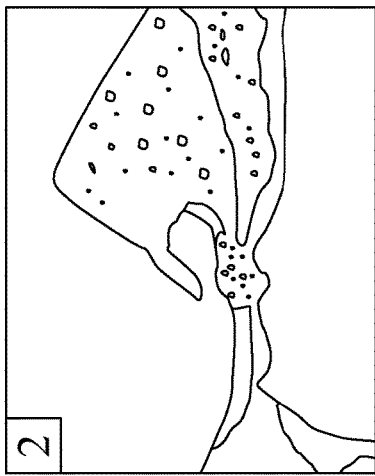
Figure 10A:
Figure 10E:
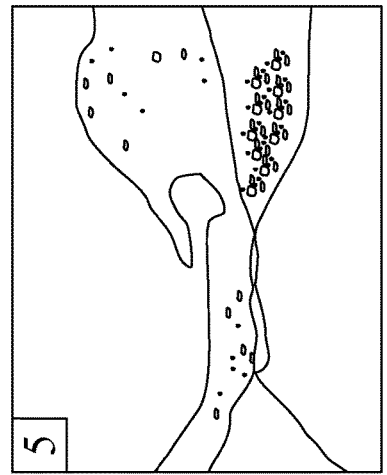
Figure 10D:
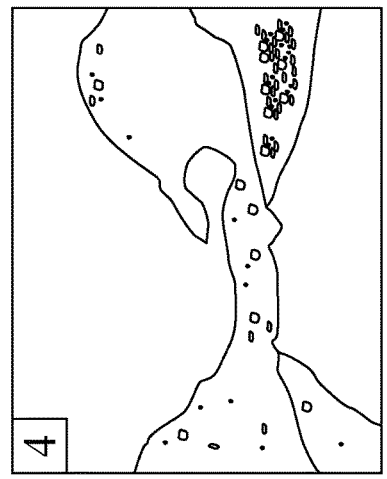

FIG. 9 shows a cross-section view through the basal turn of the mouse scala tympani following PDMS implantation revealing significant scar tissue formation at 22 weeks (outlined in red). PDMS track was marked with asterisk. Hearing and histological responses to two different PDMS materials were compared in mouse cochlea. Both PDMS materials induced significant fibrosis in the scala tympani in the implanted ears (FIG. 9), similar to the response to cochlear implants in humans and other rodent models. A similar rat model was used to compare the response of cochlear tissues to coated and uncoated PDMS implants. PDMS may be activated using a benzophenone-acetone soak and platinum may be activated using a methacrylic acid wash, then both types of substrates may be dipped in CBMA monomer solution and evenly UV irradiated on all sides under dry nitrogen in order to polymerize the coating. Substrates may then be rinsed in sterile saline and allowed to remain moist until use.

Prior to implantation, implants may be UV irradiated under a bactericidal lamp to sterilize. The left cochlea may be implanted with coated or uncoated about 3 mm long×0.5 mm wide slips of PDMS or about 3 mm long platinum-iridium wires with a diameter of about 0.5 mm using a dorsal approach with insertion of the implant through round window. Animals were divided into four groups of 6 as described in Table 1.

TABLE 1

| | Uncoated | CBMA coated |
|---|---|---|
| PDMS implant | 6 | 6 |
| Platinum wire | 6 | 6 |

Auditory brainstem responses (ABR) and distortion product otoacoustic emissions (DPOAE) may be used to evaluate hearing preimplantation, at about 1 month and again at about 3 months, using otomicroscopy to rule out middle ear effusion prior to each testing. ABR thresholds at 4, 8, 16, and 32 kHz and DPOAE responses may be measured to determine the effect of zwitterionic coated substrates on cochlear function and whether, therefore, they may be safe for use in hearing preservation surgery.

Following audiometric testing at 3 months, animals may be sacrificed and both cochleae may be harvested and processed for histology. Briefly, the otic capsules may be removed from the temporal bone following transcardial perfusion with 4% paraformaldehyde, and were postfixed for 24 hours in 4% paraformaldehyde. They may then be decalcified in 500 mM ethylenediaminetetraacetic acid (EDTA) in PBS for 7 days or until bony tissue is adequately softened. The oval window and apex may be opened following decalcification to ensure adequate infiltration of viscous resin into the cochlear fluid spaces, and the implant may be removed from the cochlea prior to further processing. Samples may be dehydrated in an ethanol gradient followed by propylene oxide, and may be transitioned to Spurr's resin. Once in 100% Spurr's resin, samples were properly oriented in an embedding block and were heated to 60° C. overnight to polymerize. After embedding, they were bisected in the mid-modiolar plane through the round window, then re-embedded and sectioned using a glass or diamond knife.

Inflammation around coated and uncoated implants may be evaluated by immunohistochemistry. CD-68 may identify macrophages, CD20 may identify B cells, and CD3 may identify T cells as has been previously described in human temporal bones. The percent cross sectional area occupied by fibrotic tissue in the scala tympani may be measured, and the magnitude of the immune response may be quantified by counting all stained cells within the fibrotic tissue. Immune cell density may be calculated by dividing the total number of cells in the fibrotic tissue by the area occupied by fibrotic tissue. Fibrosis may be measured about 2 mm from the round window (the midpoint of the implant) and at about 5 mm from the round window (slightly past the implant), to understand where and how intracochlear fibrosis evolves. Finally, the integrity of the organ of Corti were evaluated using a morphologically-based grading system previously used in mouse and cat cochlear implant models (FIGS. 10A-10E) and neuronal survival were quantified as previously described. As shown in FIGS. 10A-10E, organ of Corti (OC) ordinal grading system is depicted with representative histologic sections at 20× magnification. Scale bar=100 μm. 5=normal OC architecture, presence of inner and outer hair cells, inner hair cell (IHC) cilia visible. 4=normal OC architecture, presence of IHC and outer hair cell (OHC), no IHC cilia visible. 3=abnormal IHC and/or OHC, tunnel of Corti open. 2=tunnel of Corti collapsed. 1=single cell layer.

Figure 11:
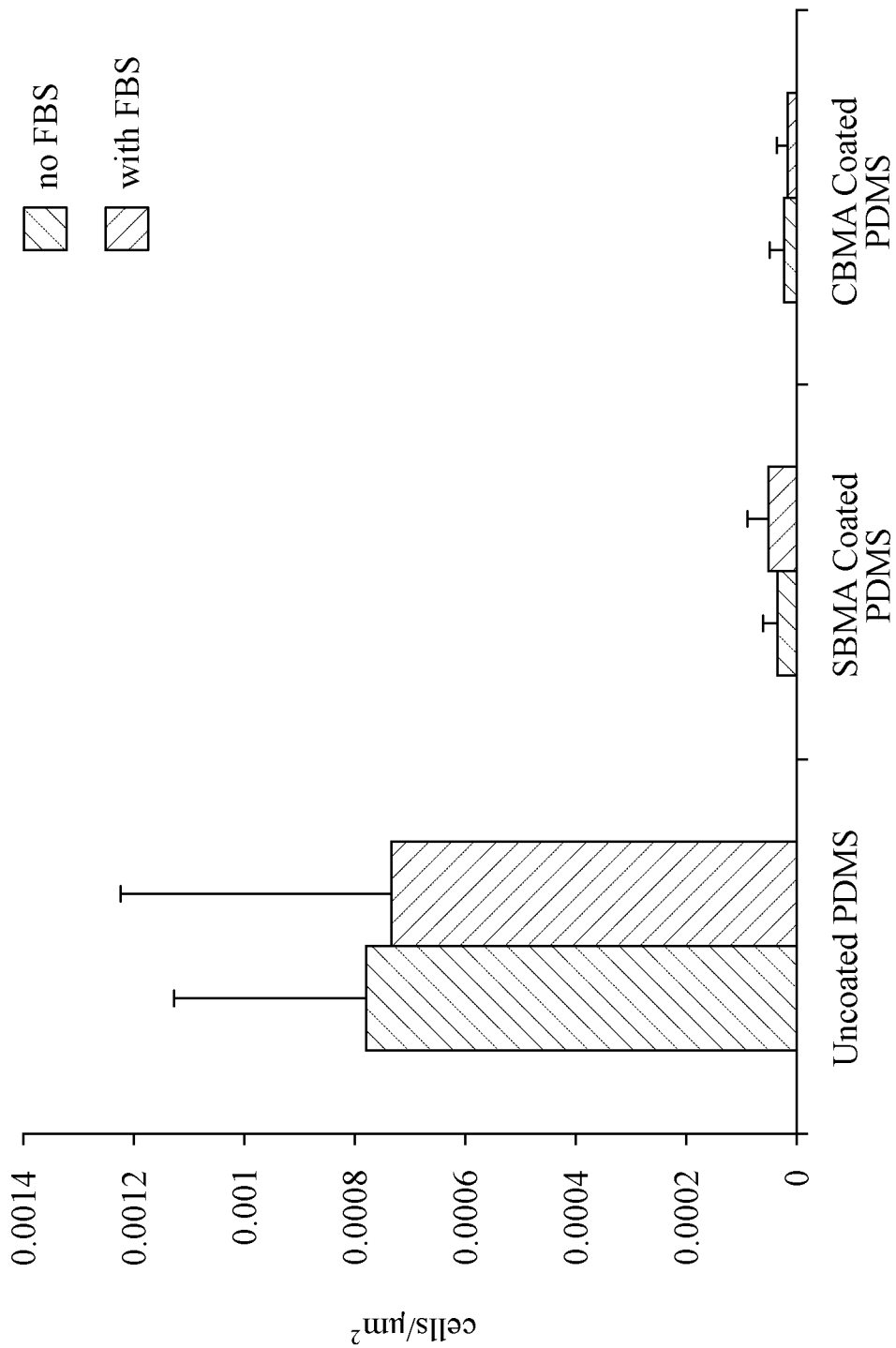
FIG. 11 illustrates that zwitterionic coatings of the present invention reduce fibroblast adhesion on a PDMS substrate, with and without pre-incubating with fetal bovine serum (FBS).

As shown in FIG. 11, zwitterionic coatings of PDMS materials (SBMA and CBMA) significantly reduced fibroblast adhesion on PDMS. With fetal bovine serum (FBS), SBMA coating can reduce more fibroblast adhesion than without FBS. Contrarily, CBMA coating can reduce more fibroblast adhesion without FBS than with FBS. Fetal bovine serum is the most widely used serum-supplement for the in vitro cell culture of eukaryotic cells. This is due to its having a very low level of antibodies and containing more growth factors, allowing for versatility in many different cell culture applications.

Anti-Bacterial: Wet Testing

Antimicrobial activity with respect to bacteria may be quantified using a colonization assay pre-incubation with 50% fetal bovine serum for 18-20 hours at 120 RPM at 37° C., which is preferred. Following pre-incubation, samples are placed in Staphylococcus aureus (S. aureus, ATCC 25923) which has been diluted from an overnight culture to a planktonic concentration of 1-3×105 CFU/mL in 1% tryptone soy broth (TSB). Samples are incubated with bacteria for 24-26 hrs with agitation (120 rpm) at 37° C. The concentration of TSB varies with the organism being used. After incubation, the samples are placed in 3 ml PBS for 5 min at 240 RPM at 37° C. to remove bacteria not tightly attached. Then accumulated bacteria on materials are removed by sonication in a new solution of PBS and the total number of bacterial cells quantified through dilution plating. Preferably at least a 1, 2, 3 or 4 log reduction in bacterial count occurs relative to colonization on a control. Similar adherence assays are known in the art for assessing platelet, cell, or other material adhesion to the surface. A surface that has a lower bacterial count compared to reference polymers may be said to reduce microbial colonization.

PDMS substrate coated with SBMA and CBMA zwitterionic coatings were subjected to anti-bacteria wet testing. Bacteria were expressed with a green fluorescent protein (GFP) cultured overnight at 37° C. Bacterial suspension in phosphate buffered saline (PBS) was incubated with the samples for 1 hour at room temperature. PDMS substrates were washed three times with PBS and were imaged with epifluorescent microscope. Number of green fluorescent protein expressing bacteria was scored.

Figure 12:
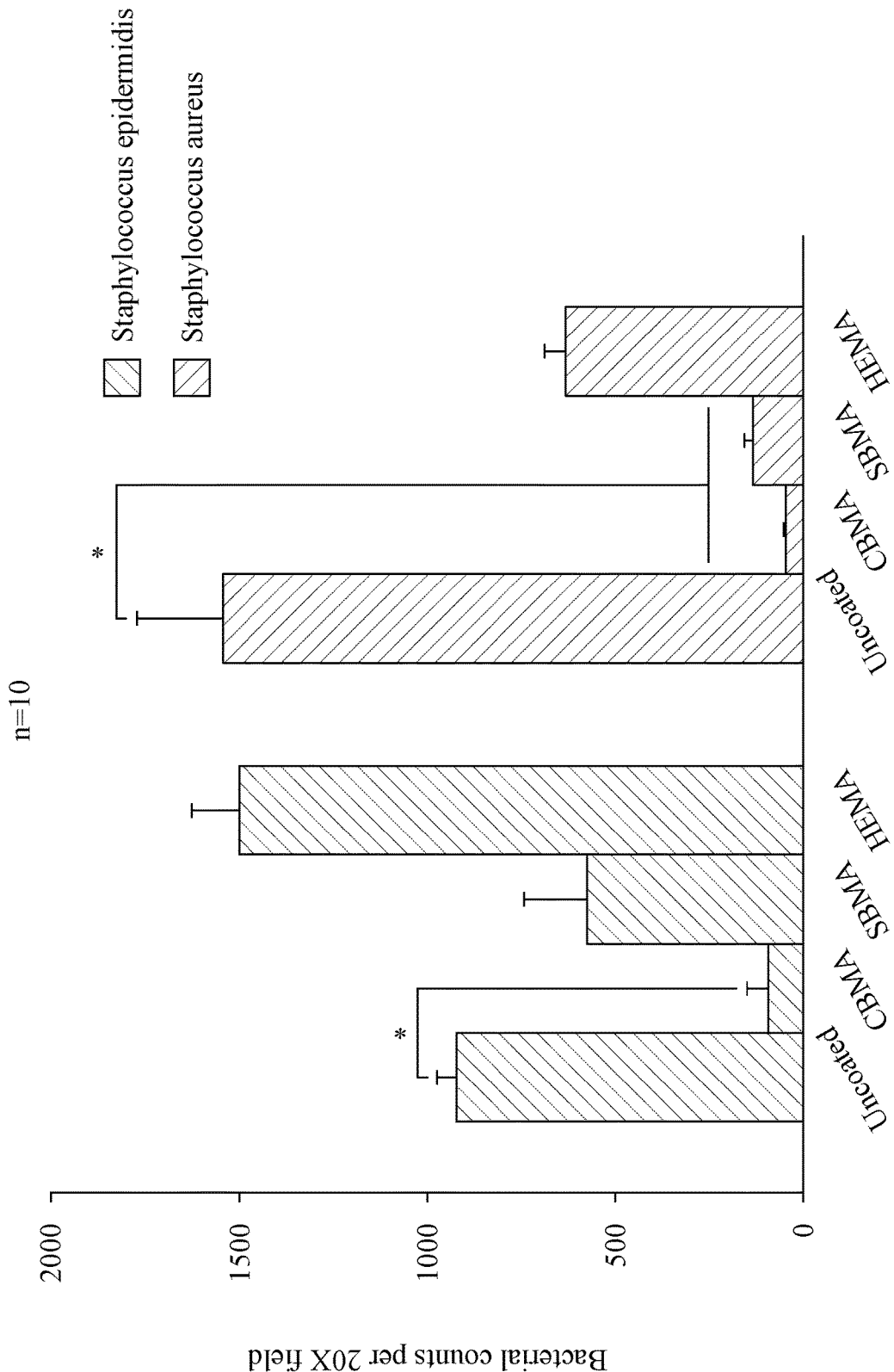
FIG. 12 illustrates that zwitterionic CBMA and SBMA coatings of the present invention on a PDMS substrate reduce S. aureus and S. epidermis adhesion on wet surfaces compared to an uncoated PDMS substrate and a hydroxyethylmethacrylate (HEMA) coated PDMS substrate.

As shown in FIG. 12, CBMA and SBMA coating of PDMS significantly reduces S. aureus and S. epidermis adhesion on wet surfaces. HEMA refers to 2-hydroxyethyl methacrylate. N refers to how many experiments were performed.

Anti-Bacterial: Dry Test

PDMS substrate coated with SBMA and CBMA zwitterionic coatings were subjected to anti-bacteria dry testing. Bacteria engineered to express a green fluorescent protein (GFP) were cultured overnight at 37° C. Bacterial suspension in phosphate buffered saline (PBS) was sprayed on the sample surface for 1 hour at room temperature. Samples were incubated for 1 hour at room temperature and washed three times with PBS. Samples were imaged with epifluorescent microscope. Number of green fluorescent protein expressing bacteria was scored.

Figure 13:
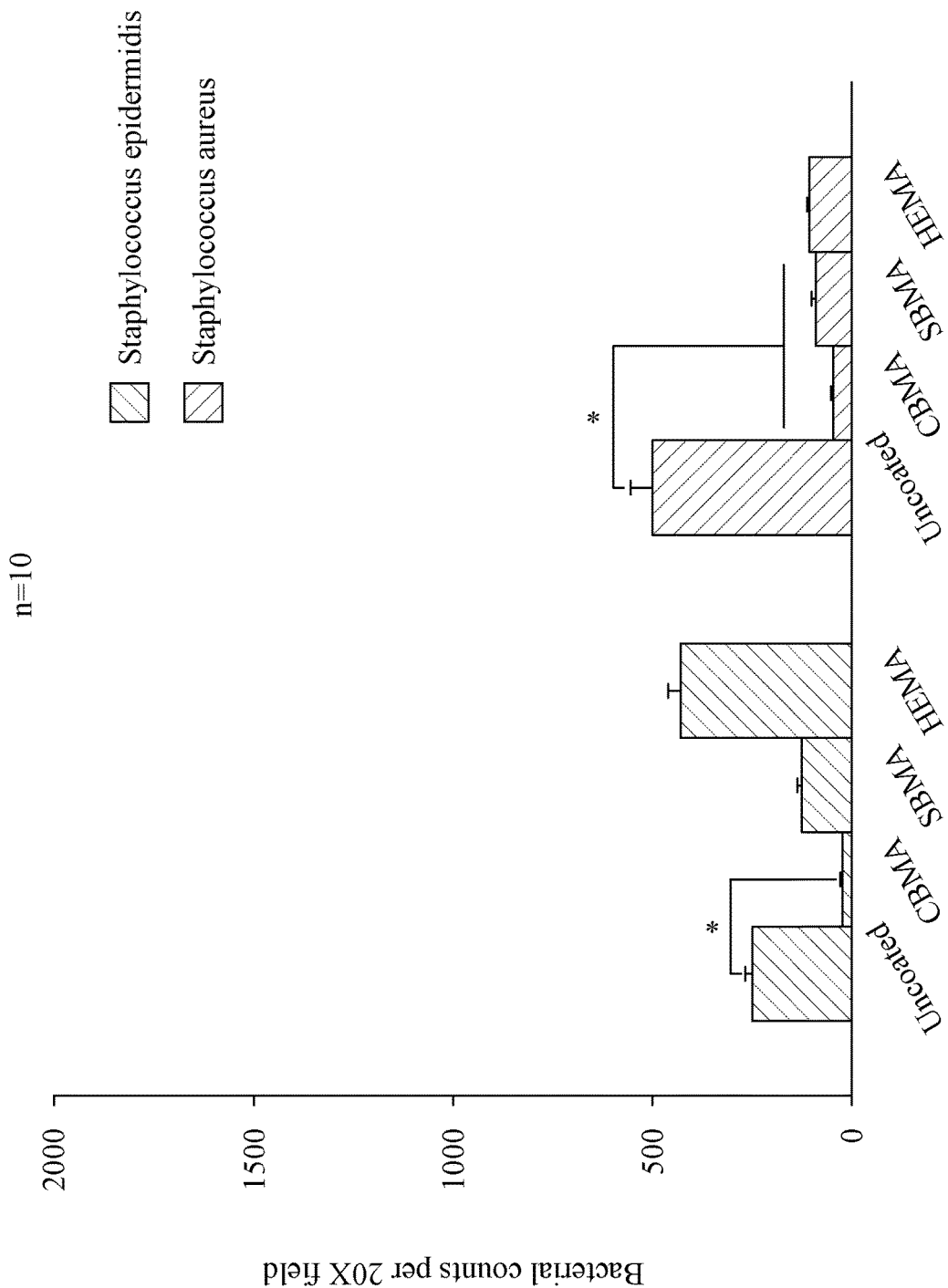
FIG. 13 illustrates that zwitterionic CBMA and SBMA coatings of the present invention on a PDMS substrate reduce S. aureus and S. epidermis adhesion on dried surfaces compared to an uncoated PDMS substrate and a HEMA coated PDMS substrate.

FIG. 13 shows that CBMA and SBMA coating of PDMS significantly reduced S. aureus and S. epidermis adhesion on dried surfaces.

Anti-Bacterial: 24 Hour Incubation

PDMS substrate coated with SBMA and CBMA zwitterionic coatings were subjected to anti-bacteria 24 hour incubation testing. Bacteria engineered to express a green fluorescent protein (GFP) were cultured overnight at 37° C. The sample surface was blocked by FBS 37° C. for 1 hour. Samples were washed three times with PBS. Bacteria suspension in PBS was incubated with samples for 24 hour at 37° C. Samples were washed three times with PBS and were imaged with epifluorescent microscope. Number of green fluorescent protein expressing bacteria was scored.

Figure 14:
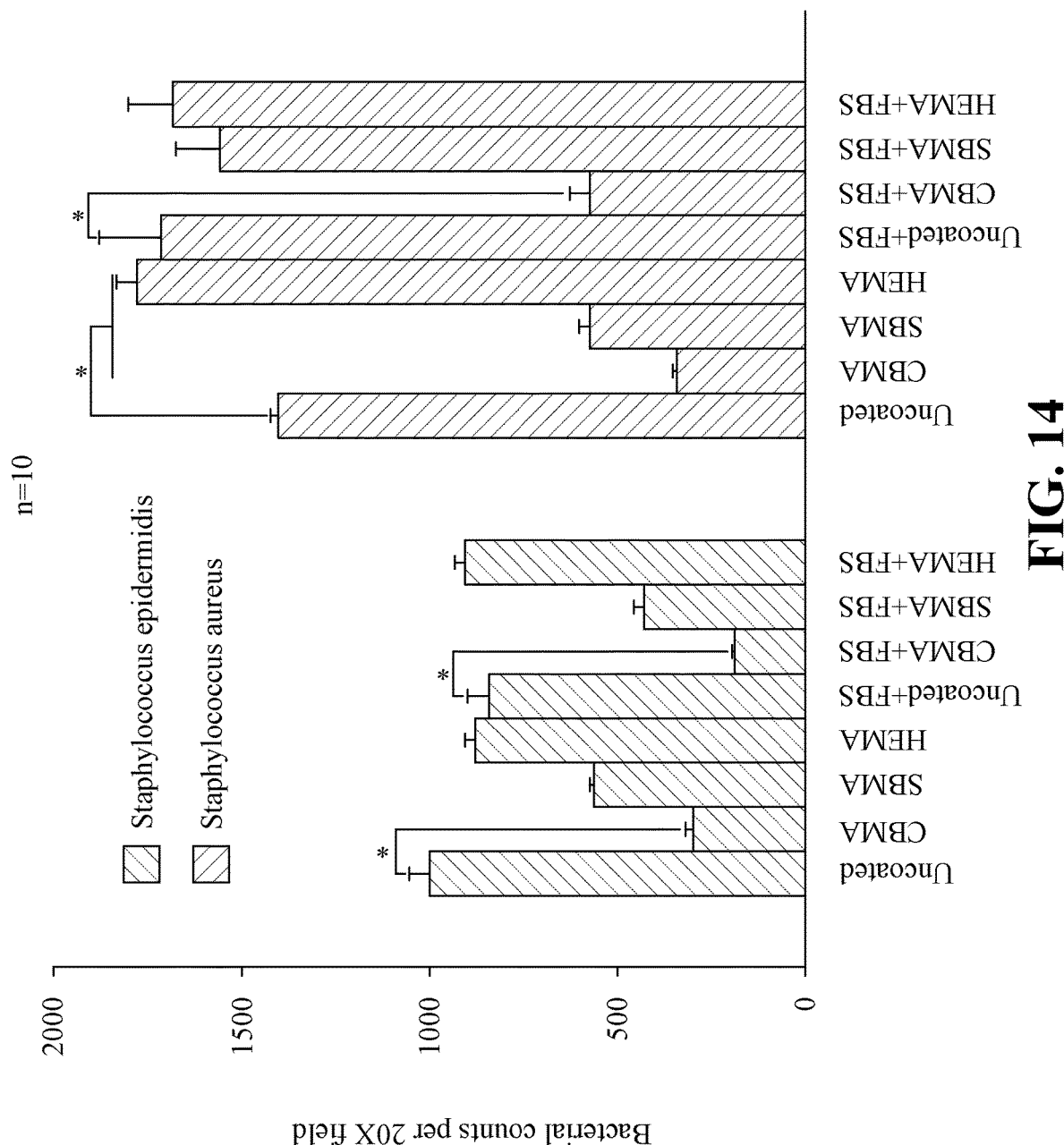
FIG. 14 illustrates that zwitterionic CBMA and SBMA coatings of the present invention on a PDMS substrate reduce S. aureus and S. epidermis adhesion in vitro at 24 hrs. compared to an uncoated PDMS substrate and a HEMA coated PDMS substrate, with and without pre-incubating with fetal bovine serum (FBS).

FIG. 14 shows that CBMA and SBMA coating of PDMS polymer significantly reduced S. aureus and S. epidermis adhesion under 24 hour incubation. SBMA and CBMA coated surfaces have reduced S. aureus adhesion on the dried surface compared to the uncoated surface. However, HEMA did not reduce adhesion of S. epidermidis on the dried surface compared to the uncoated surface.

Anti-Bacterial: 48 Hour Incubation

Bacteria engineered to express a green fluorescent protein (GFP) were cultured overnight at 37° C. The sample surface was blocked by FBS 37° C. for 1 hour. Samples were washed three times with PBS. Bacteria suspension in PBS was incubated with samples for 48 hour at 37° C. Samples were washed three times with PBS. Samples were imaged with epifluorescent microscope. Number of green fluorescent protein expressing bacteria was scored.

Figure 15:
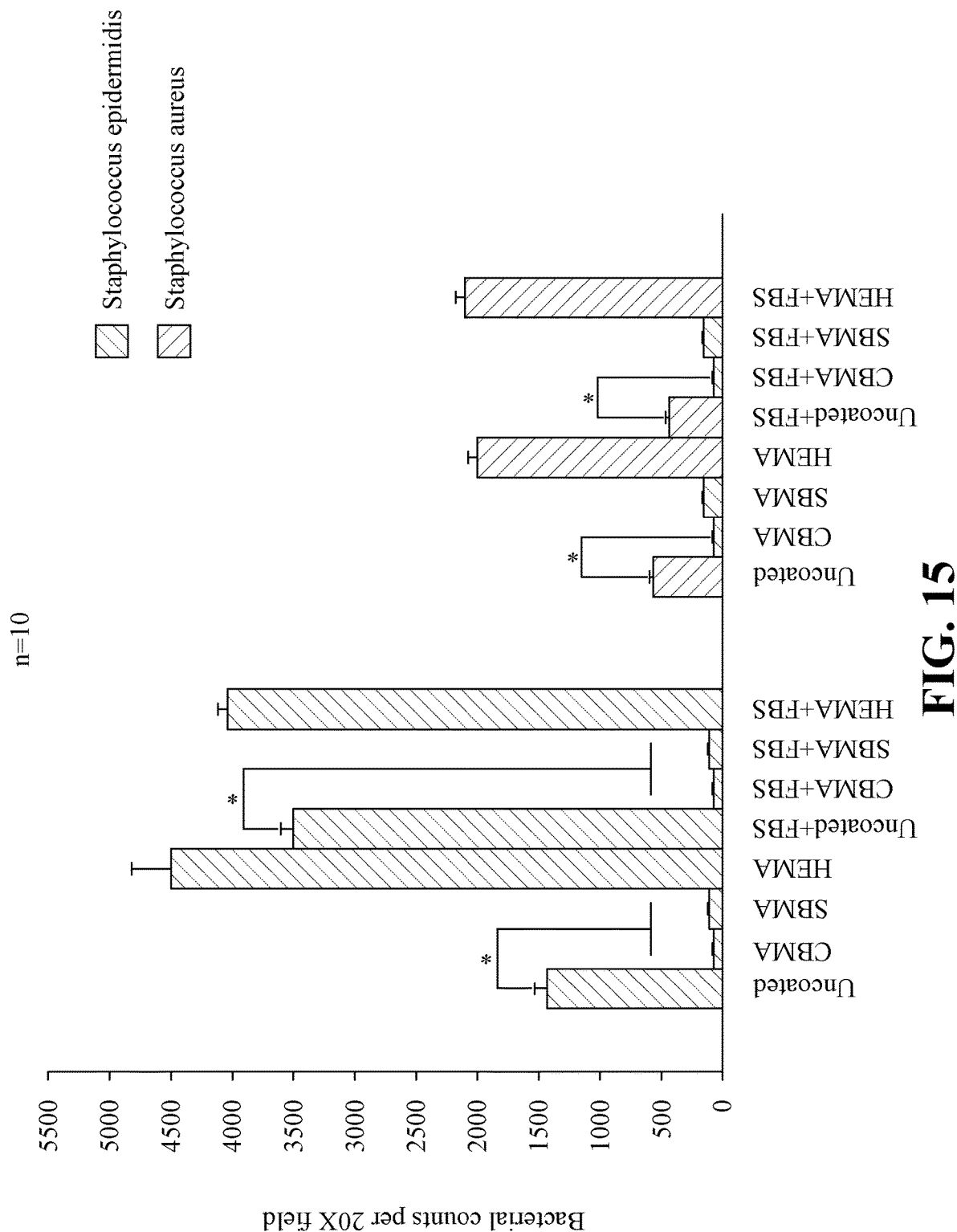
FIG. 15 illustrates that zwitterionic CBMA and SBMA coatings of the present invention on a PDMS substrate reduce S. aureus and S. epidermis adhesion in vitro at 48 hrs. compared to an uncoated PDMS substrate and a HEMA coated PDMS substrate, with and without pre-incubating with fetal bovine serum (FBS).

FIG. 15 shows that CBMA and SBMA coating of PDMS significantly reduced *S. aureus* and *S. epidermis* adhesion under 48 hour incubation compared to plain surface.

Figure 16:
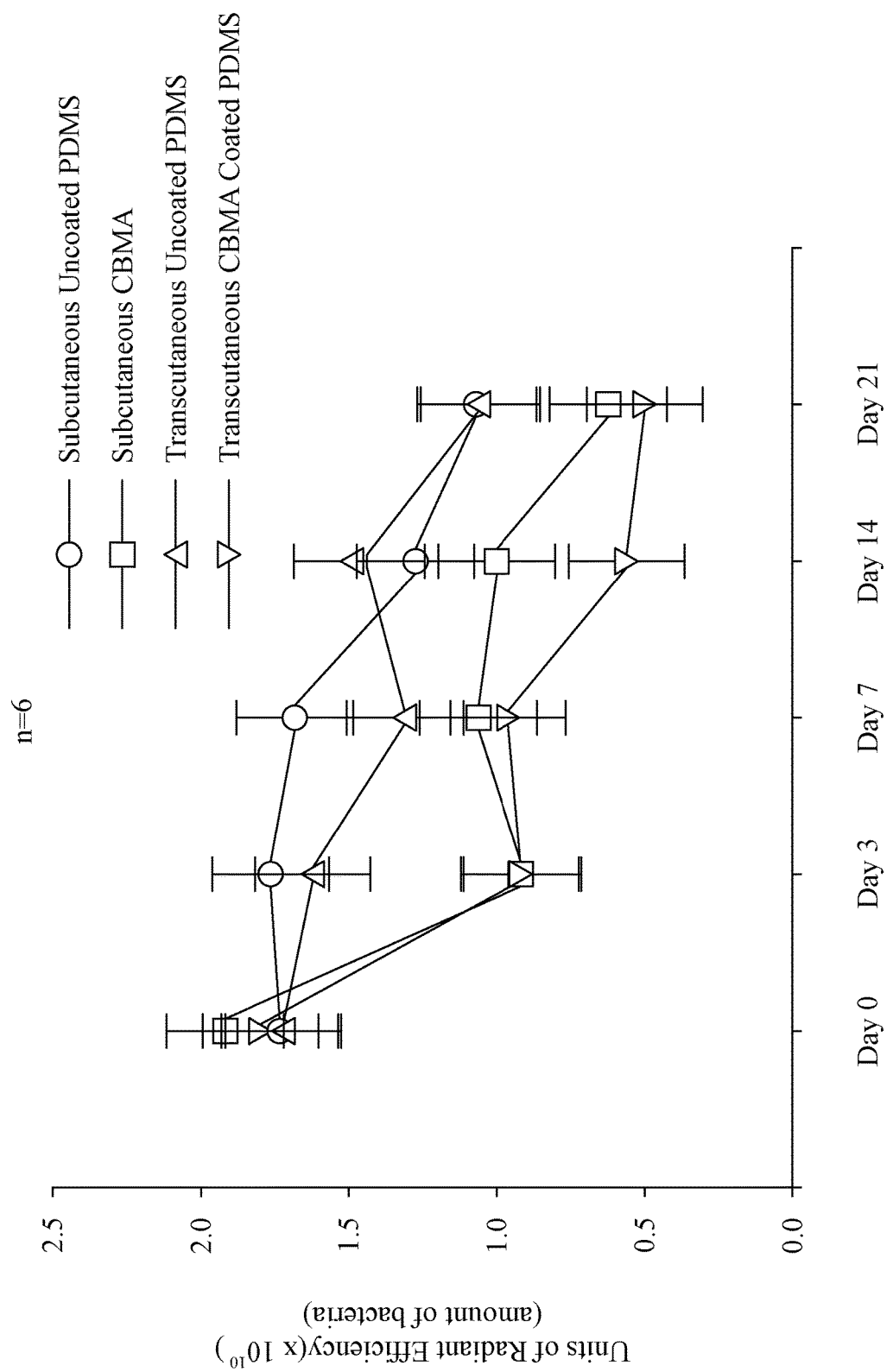
FIG. 16 is a graphical representation showing the amount of S. aureus colonization for subcutaneous and transcutaneous CBMA-coated PDMS implants in rats, according to the present invention, compared to subcutaneous and transcutaneous uncoated PDMS implants.

In Vivo Experiment for Anti-Bacterial Colonization of Trans- and Sub-Cutaneous PDMS Implants PDMS substrates coated with SBMA and CBMA zwitterionic coatings were subjected to bacteria colonization of trans- and sub-cutaneous PDMS implants testing. Bacteria (*S. aureus*) engineered to express a green fluorescent protein (GFP) were cultured overnight at 37° C. The bacteria with concentration about $10^8$/ml. Live image was injected adjacent to PDMS implants with or without CBMA coating and placed either subcutaneously or transcutaneously. A live imaging system was used to detect the GFP signal. As shown in FIG. 16, at day 0, units of radiant efficiency were all the same at $P>0.05$. Thereafter the CBMA coated PDMS implants demonstrated reduced bacterial fluorescence signal compared to uncoated PDMS implants.

Bacterial Counts and Biofilm Assessment

Figure 17:
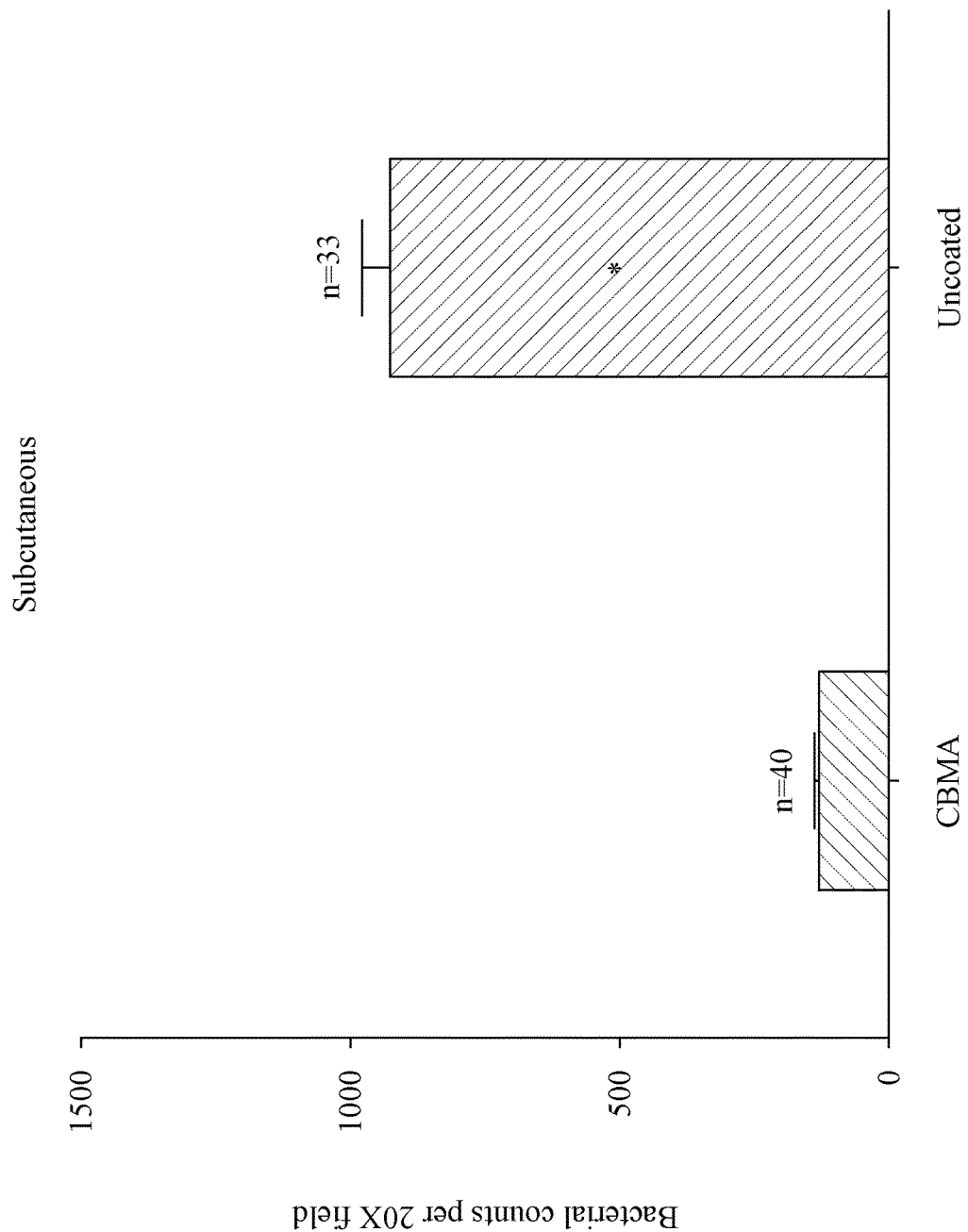
FIG. 17 is a graphical representation of the amount of S. aureus adhesion, after removal, for subcutaneous CBMA-coated PDMS implants, according to the present invention, compared to subcutaneous uncoated PDMS implants.

Digital epifluorescent images were captured on a Leica DMIRE2 microscope (Leica Microsystems, Bannockburn, IL) with Leica DFC350FX digital camera and Metamorph software (Molecular Devices, Silicon Valley, CA). Pictorial results of confocal laser scanning microscope studies of biofilm attachment assays were also obtained. FIG. 17 has shown that CBMA coating of subcutaneous PDMS implants reduced *S. aureus* colonization. The counts for CBMA coating had less than 250 GFP-expressing *S. aureus* bacteria compared to uncoated substrate of close to 1,000 GFP-expressing *S. aureus* bacteria.

Figure 18:
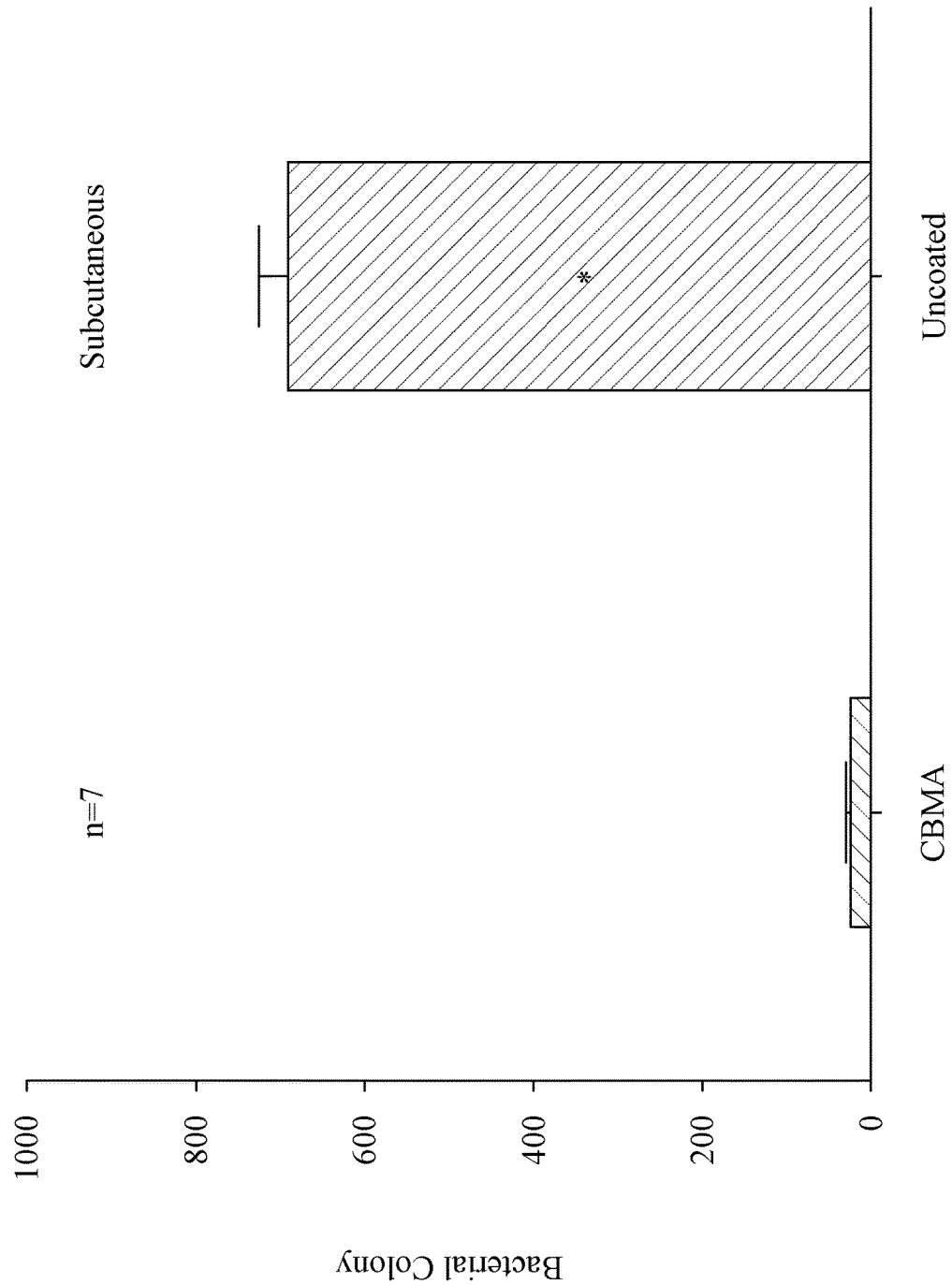
FIG. 18 is a graphical representation of the amount S. aureus colonies cultured from a subcutaneous implant at the time of removal, for CBMA-coated PDMS, according to the present invention, compared to uncoated PDMS.

FIG. 18 has shown that CBMA coating of subcutaneous PDMS implants reduced *S. aureus* colonization after removal from implantation. The counts for CBMA coating had less than 100 GFP-expressing *S. aureus* bacteria compared to uncoated substrate of close to 700 GFP-expressing *S. aureus* bacteria.

In Vitro Experiment for Platelet Adhesion

Fresh rat blood were extracted and mixed with the 3.8 wt % sodium citrate solution at a dilution ratio of 9:1 (v/v). Platelet-rich plasma (PRP) was separated from the whole blood by centrifuging at 1000 rpm/3500 rpm each for 15 min. PRP solution was incubated with the PDMS substrate coated with SBMA and CBMA zwitterionic coatings or uncoated PDMS substrate for 60 min at 37° C. The PDMS substrates were washed by PBS and fixed with 4% PFA for 30 min. The sample was washed again with PBS. The sample was stained for 60 min with Alexa Fluor 488 Phallodin (1:250). An epifluorescence microscope was used to take the images.

Figure 19:
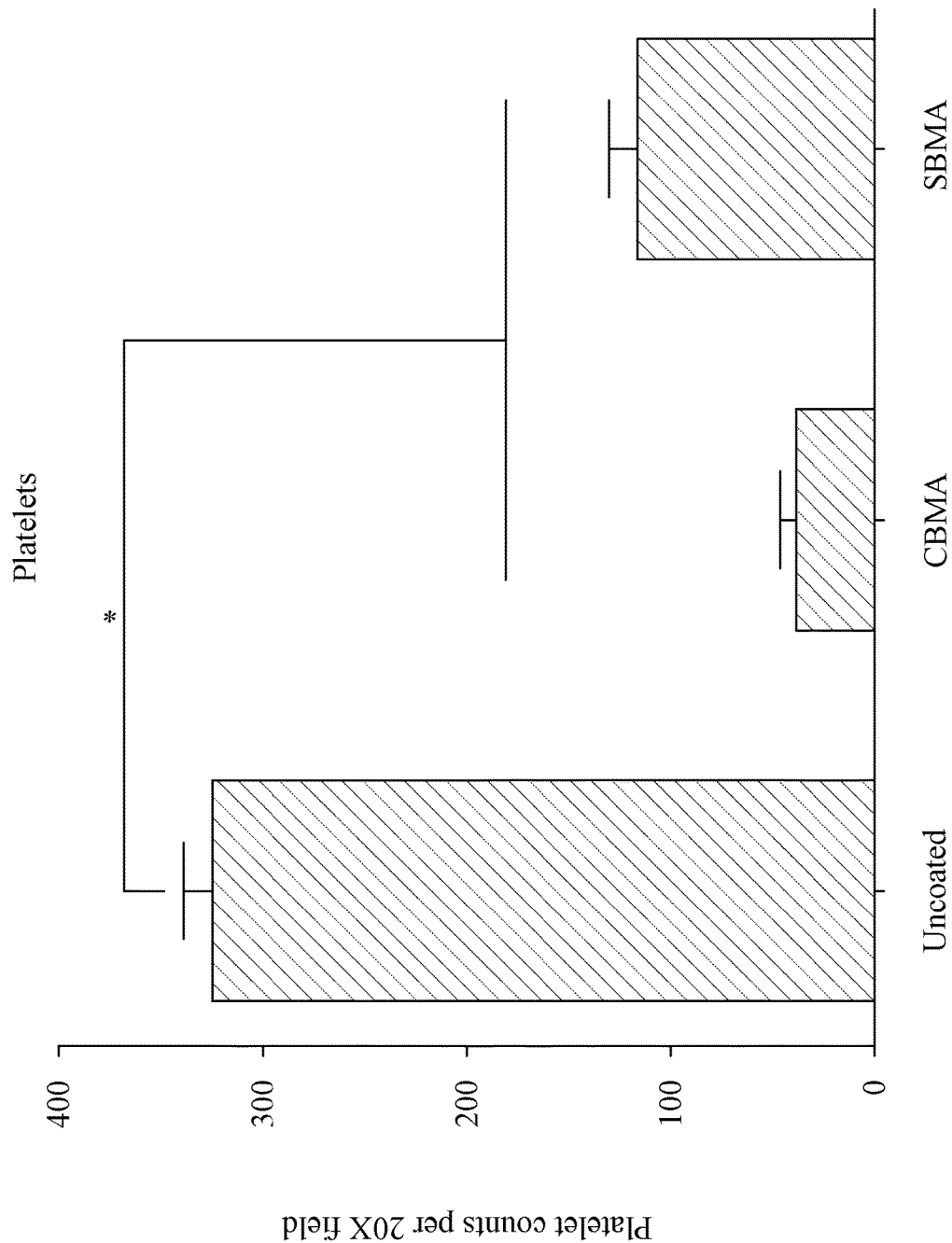
FIG. 19 is a graphical representation of the amount of platelet adhesion for CBMA-coated and SBMA-coated PDMS, according to the present invention, compared to uncoated PDMS.

FIG. 19 has shown that CBMA and SBMA coatings significantly reduced platelet adhesion compared to plain uncoated substrate.

In Vivo Experiment for Platelet Adhesion/Thrombus Formation

Figure 20A:
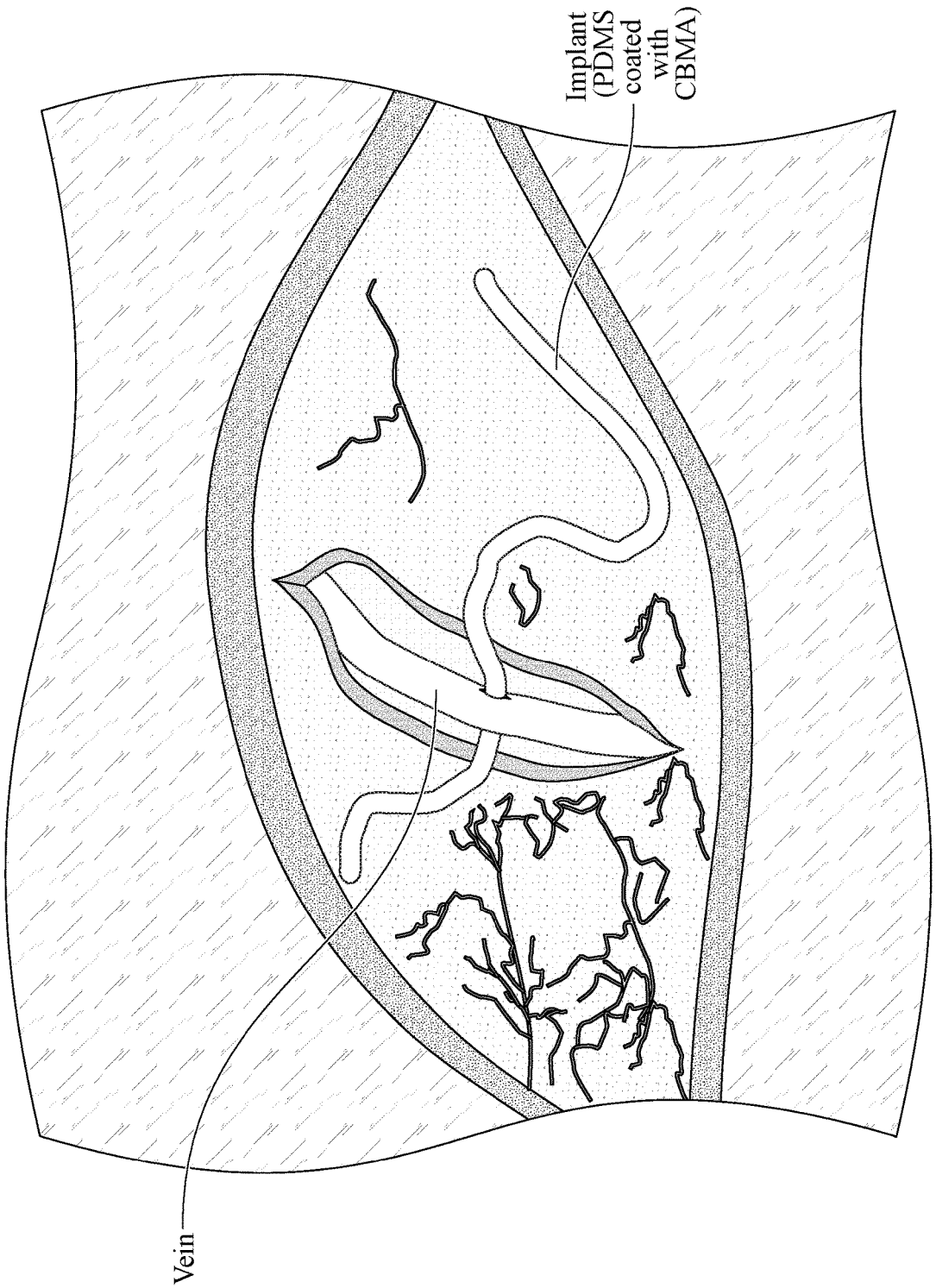
FIG. 20A illustrates an in vivo experiment for thrombus formation on a CBMA-coated PDMS implant in a rat femoral vein.
Figure 20B:
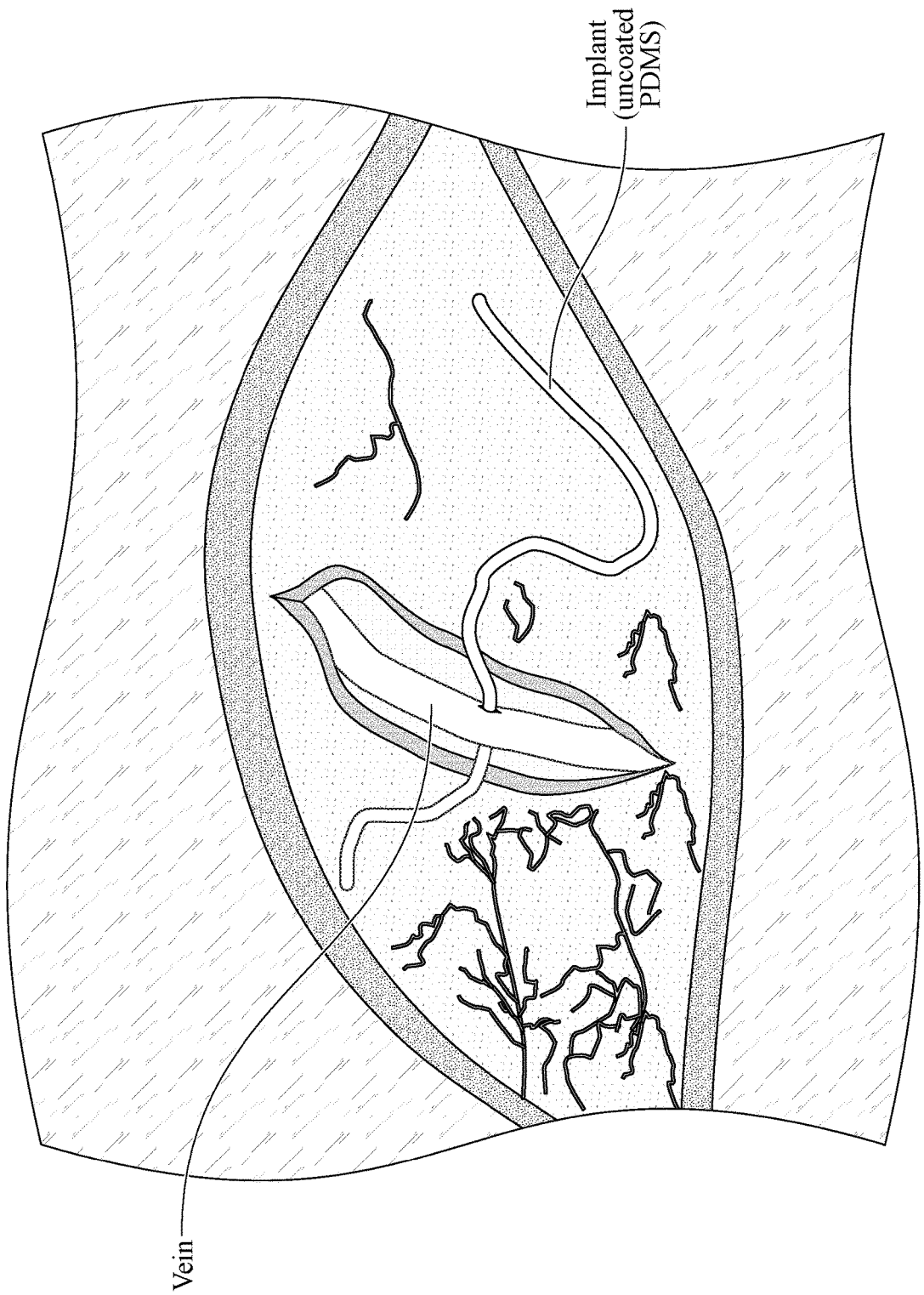
FIG. 20B illustrates an in vivo experiment for thrombus formation on an uncoated PDMS implant in a rat femoral vein.

FIG. 20B shows a conventional PDMS implant placed in the femoral vein of a rat. FIG. 20A shows the same implant, this time coated with the coating of the invention. The cross linked coating forms a zwitterionic hydrogel which is highly water absorbent and swells to form a slippery, gelatinous covering. Nevertheless, the method of attachment of the coating to the PDMS substrate makes the coating durable, such that it does not detach from the implant. Moreover, the shear strength of the bond is greater than the shear strength of the coating itself so that the coating will not peel off under shear stress. FIG. 20A shows a coating of exaggerated thickness. In practice, the coating can be substantially thinner and still retain the advantageous properties of the invention. In some embodiments, the thickness of the cross-linked coating may be at least about 100 nm. In another embodiment, the thickness of the cross-linked coating may be at least about 150 nm, about 200 nm, about 250 nm, about 260 nm, about 270 nm, about 280 nm, about 2900 nm, about 300 nm, about 330 nm, for example. In some embodiments, the crosslinked coating may be at least about one micron. In other embodiments, the crosslinked coating may be at least about 1 mm.

Figure 21:
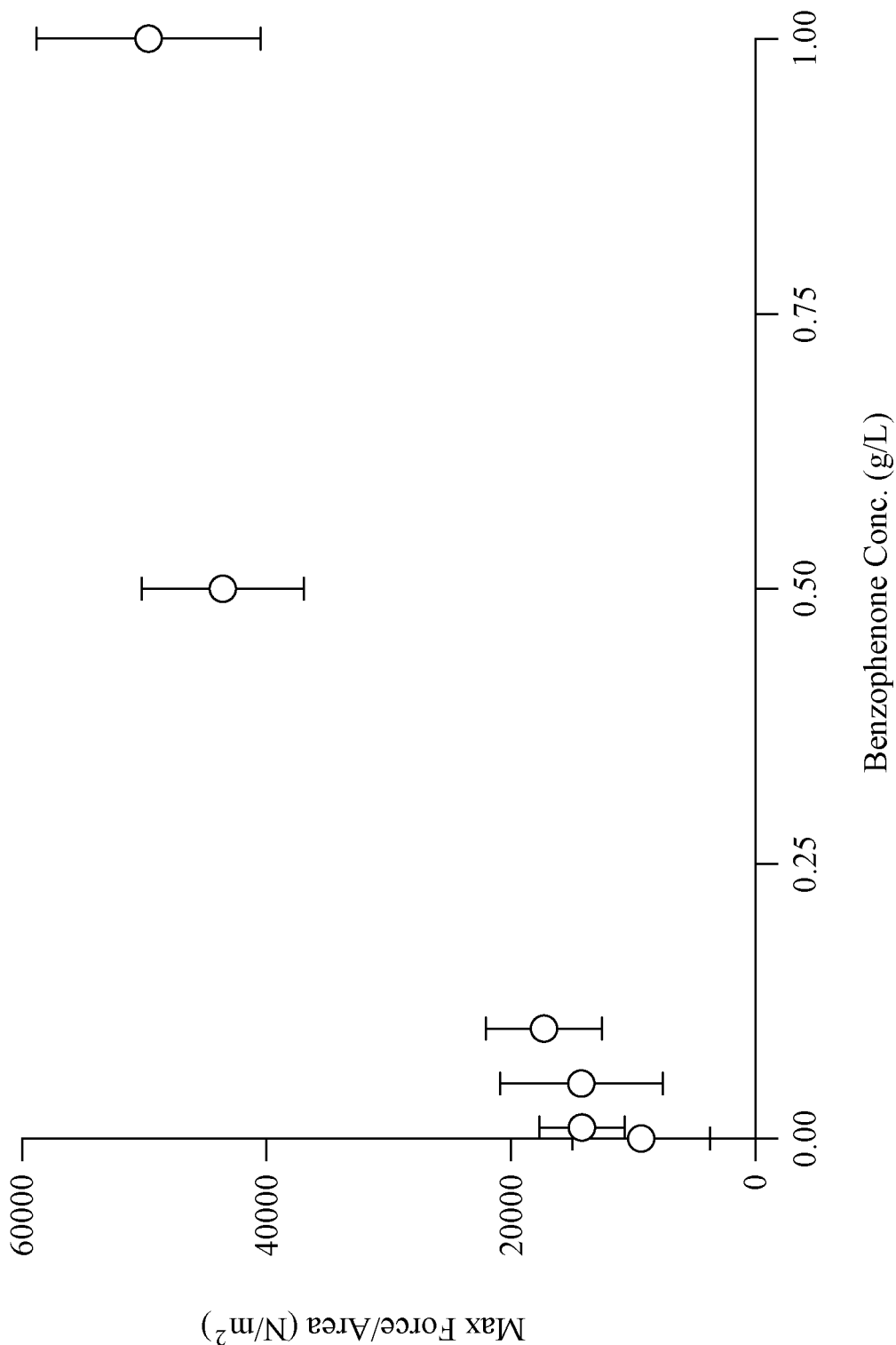
FIG. 21 is a graphical representation of the adhesion (measured with a shear adhesion test) of zwitterionic cross-linked SBMA hydrogel polymers to a PDMS polymer substrate, as a function of the concentration of the benzophenone solution used in the coating process.

FIG. 21 showed that there strong dependence on benzophenone concentration (the solution concentration of benzophenone dissolved in acetone used to apply the benzophenone to the surface) to adhesion (max force per area). At low concentrations of benzophenone, the adhesion to the PDMS substrate is weak resulting in lower max force per area required to fracture the substrate. As the solution concentration is increased, adhesion is stronger evidenced by the higher max force per area required to fracture the sample. Higher concentrations of benzophenone allow a larger number of covalent bonds to form between the zwitterionic network and the PDMS substrate resulting in a stronger grafting to the PDMS.

Figure 22:
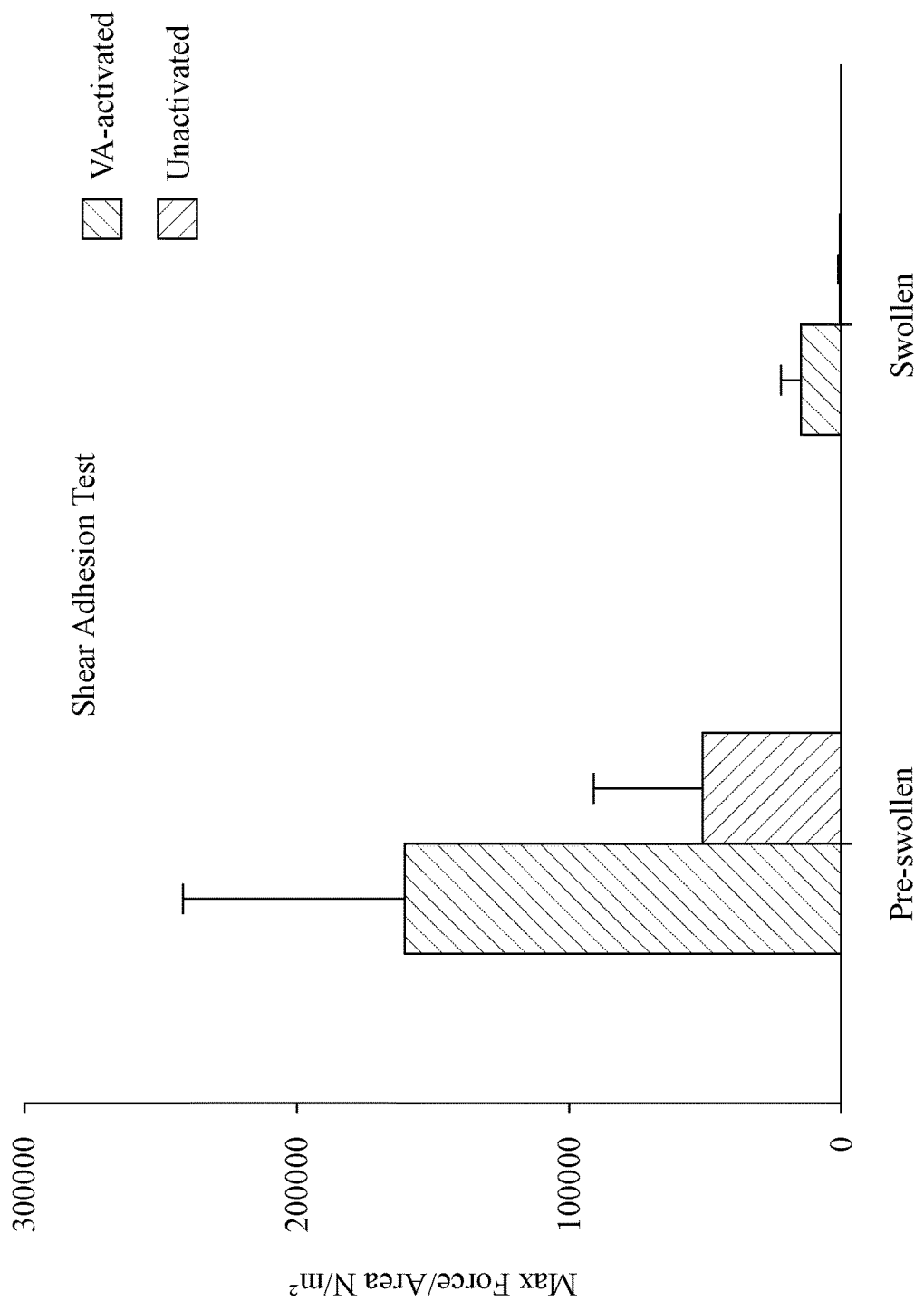
FIG. 22 is a graphical representation of the adhesion (measured with a shear adhesion test) of zwitterionic cross-linked SBMA hydrogel polymers (swollen (i.e., after soaking in water for 24 hrs) and unswollen (i.e., directly after polymerization)) to a stainless steel substrate, with and without activation of the substrate surface using vinylphosphonic acid (VA).

As shown FIG. 22, shear adhesion testing has shown that SBMA crosslinked films demonstrate stronger adhesion to a vinyl phosphonic acid (VA)-activated pre-swollen stainless steel substrate compared to unactivated (bare metal) samples.

Figure 23:
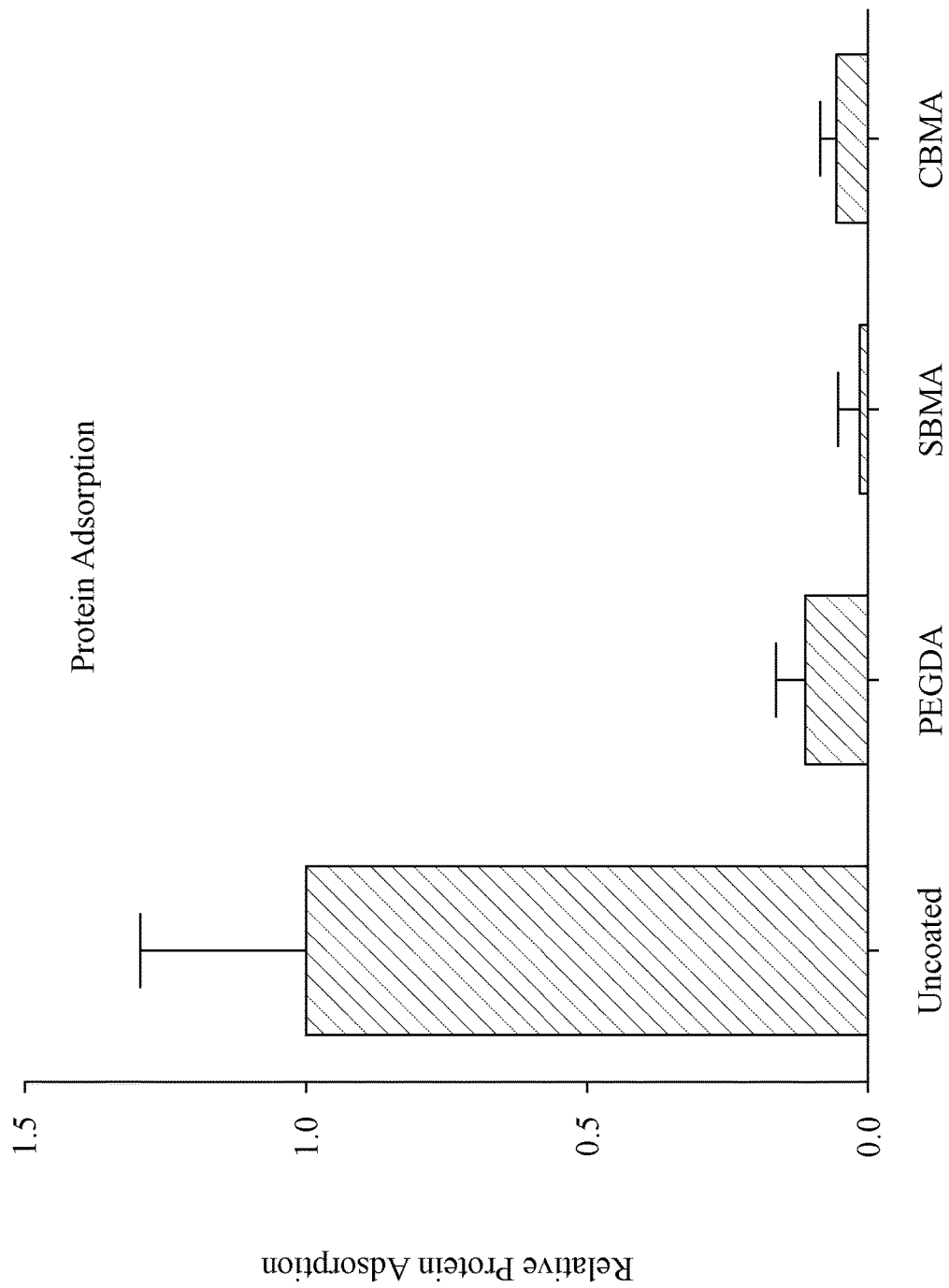
FIG. 23 is a graphical representation of protein adsorption on PDMS surfaces with zwitterionic CBMA and SBMA coatings, according to the present invention, and a PEGDA coating, as indicated by fluorescence intensity relative to an uncoated PDMS control surface.

As shown in FIG. 23, PDMS substrate coated with SBMA and CBMA zwitterionic coatings were subjected to protein adsorption testing. SBMA and CBMA-coated PDMS surfaces significantly reduced nonspecific protein adsorption compared to uncoated PDMS and polyethyleneglycol diacrylate (PEGDA). Uncoated PDMS was used as a baseline control. The SBMA coated surface adsorbed the least amount of nonspecific protein. The CBMA coated surface adsorbed the second least amount of protein. The PEGDA coated surface was adsorbed more than either SBMA or CBMA coated surfaces.

The durability of zwitterionic coatings in vivo may be evaluated by determining the amount of coating that remains on the implant at 3 months. To quantify the amount of coating that remains following implantation, the ability of zwitterionic coatings to hold water may be used. Implants were explanted prior to processing for histology and a water-soluble dye absorption assay was employed. Coated and uncoated PDMS and platinum pieces that had not been implanted may serve as a control. Implants may be incubated in a solution of water-soluble dye, quickly rinsed and then allowed to equilibrate with a small volume of solution. Spectrophotometry may then determine the concentration of dye in solution, which may serve as an indirect measure of the amount of coating remaining on the implant. Implants may also be visually inspected following dye incubation to evaluate the uniformity of coating. These results of these studies establish the durability of zwitterionic thin film coatings on implant materials and their ability to significantly reduce intracochlear fibrosis.

Zwitterionic coated PDMS and platinum substrates may reduce fibrosis and hearing loss compared to uncoated PDMS and platinum substrates, and histological examination of implanted cochleae may show considerably less fibrosis around coated implants than uncoated implants. Bare platinum wire may produce less fibrosis than PDMS, based on data from a previous study done in mice. A threefold reduction in the cross sectional area of fibrotic tissue within the scala tympani would be biologically meaningful, although based on results from subcutaneous bulk implantation of zwitterionic hydrogel, a much larger difference, in the range of 2-3 orders of magnitude may be expected. Organ of Corti architecture may not be significantly distorted adjacent to the implant reflected by preservation of hearing thresholds and histologically. Finally, based on the durability of other thin film coatings engineered with similar methods, zwitterionic coating may remain intact on the substrates. These results indicate that these implants are safe, durable, and beneficial for use in hearing preservation cochlear implants, and provide strong justification for moving forward with applying the technology to cochlear implant electrode arrays.

Additionally, the process of adhering the zwitterionic polymer to metals has also been demonstrated. The metal surface is first heated to high temperatures to generate a metal oxide layer on the surface. The samples are then exposed to oxygen plasma to oxidize any remaining organics. A phosphoric acid (or other appropriate acid) containing monomer with a polymerizable double bond (such as a vinyl or methacrylate group) is applied to the surface. The acid group binds the monomer chemically to the surface. Examples of appropriate monomers include vinyl phosphonic acid or any phosphonic acid (meth)acrylate. The samples are subsequently rinsed with ethanol to remove residual unbound monomer. The zwitterionic monomer solution with photoinitiator is then applied to the surface and photopolymerized to covalently graft the crosslinked film to the metal surface.

While one application of this technology is thin coatings of cochlear implant materials, the results are generally applicable to a wide variety of non-implanted and implated medical devices, including other neural prostheses, intravascular stents, in-dwelling catheters, cosmetic implants, among others. Many medical implants face similar issues including inflammation, fibrosis, thrombosis, and bacterial adhesion. The present technology stands to significantly affect medical device development and use.

It should be understood that the foregoing description relates to exemplary embodiments of the invention and that modifications may be made without departing from the spirit and scope of the invention as set forth in the following claims. Modifications and variations are possible without departing from the scope of the invention defined in the appended claims. Although some aspects of the present disclosure are identified herein as preferred or particularly advantageous, it is contemplated that the present disclosure is not necessarily limited to these aspects.

One or more of the following claims utilize the term "wherein" as a transitional phrase. For the purposes of defining the present disclosure, it is noted that this term is introduced in the claims as an open-ended transitional phrase that is used to introduce a recitation of a series of characteristics or elements and should be interpreted in like manner as the more commonly used open-ended preamble term "comprising."

Recitations of "at least one" component, element, etc., should not be used to create an inference that the alternative use of the articles "a" or "an" should be limited to a single component, element, etc.

Terms like "preferably," "commonly," "significantly," and "typically," when utilized, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

In this disclosure the terms "substantially" and "approximately" are utilized to represent the inherent uncertainty that may be attributed to any quantitative comparison, value, measurement, or other representation. The terms "substantially" and "approximately" are also utilized to represent the degree by which a quantitative representation may vary from a stated reference without resulting in a change in the basic function of the subject matter at issue.

While the invention has been described regarding a few embodiments, those skilled in the art, having benefit of this disclosure, will appreciate that other embodiments can be devised that do not depart from the scope of the invention as disclosed herein.

The invention claimed is:

1. An implantable system, comprising:
a substrate having at least one outer surface;
a photopolymerized zwitterionic hydrogel coating covalently bonded to at least a portion of the outer surface, wherein the photopolymerized zwitterionic hydrogel coating comprises zwitterionic monomer units and a crosslinker selected from the group consisting of ethylene glycol dimethacrylate (EGDMA), poly(ethylene glycol) di(meth)acrylate (PEGD(M)A), propylene glycol diacrylate, bisphenol A ethoxylate diacrylate, N,N'-methylenebis acrylamide, pentaerythritol tetraacrylate, 1,3-butylene glycol dimethacrylate (BGDMA), 1,4-butane diol diacrylate (BDDA), 1,6-hexane diol diacrylate (HDDA), hexanediol dimethacrylate (HDDMA), 1-carboxy-N-methyl-N-di(2-methacryloyloxy-ethyl) methanaminium inner salt (CBMX), neopentylglycol diacrylate (NPGDA), and trimethylolpropane triacrylate (TMPTA), and wherein the photopolymerized zwitterionic hydrogel coating is configured to resist adhesion by biomolecules, cells, tissue or bacteria.

2. The implantable system of claim 1, wherein the substrate is a component of a cochlear implant.

3. The implantable system of claim 1, wherein the zwitterionic monomer unit contains a phosphoryl choline moiety, a sulfobetaine moiety, a carboxybetaine moiety, or combinations thereof.

4. The implantable system of claim 3, wherein the zwitterionic monomer unit is carboxybetaine (meth)acrylate, phosphoryl choline (meth)acrylate, sulfobetaine (meth)acrylate, carboxybetaine (meth)acrylamide, or sulfobetaine (meth)acrylamide.

5. The implantable system of claim 1, wherein at least a portion of the outer surface of the substrate is formed from a polymeric material, and the photopolymerized zwitterionic hydrogel coating is covalently bonded to the polymeric material.

6. The implantable system of claim 5, wherein the polymeric material is polydimethyl siloxane.

7. The implantable system of claim 1, wherein the at least one outer surface of the substrate has uncoated regions, and the uncoated regions and the photopolymerized zwitterionic hydrogel coating form a micropattern on the outer surface of the substrate.

8. The implantable system of claim 7, wherein the micropattern is configured to direct cell growth of one or more of neurite cells, fibroblast cells, or glial cells on the uncoated regions.

9. The implantable system of claim 1, wherein the photopolymerized zwitterionic hydrogel coating has a thickness of at least about 100 nm.

10. The implantable system of claim 1, wherein the zwitterionic monomer unit comprises carboxybetaine methacrylate (CBMA) or sulfobetaine methacrylate (SBMA).

11. The implantable system of claim 1, wherein the photopolymerized zwitterionic hydrogel coating is covalently bonded to the at least one portion of the surface with a first photo initiator and is cross-linked by a second photo initiator.

12. The implantable system of claim 11, wherein the first photo initiator and the second photoinitiator are simultaneously photoactivated by a light source.

13. A cochlear implant comprising:
a substrate having at least one outer surface;
a photopolymerized zwitterionic hydrogel coating covalently bonded to at least a portion of the outer surface, wherein the photopolymerized zwitterionic hydrogel coating comprises zwitterionic monomer units and a crosslinker selected from the group consisting of ethylene glycol dimethacrylate (EGDMA), poly(ethylene glycol) di(meth)acrylate (PEGD(M)A), propylene glycol diacrylate, bisphenol A ethoxylate diacrylate, N,N'-methylenebis acrylamide, pentaerythritol tetraacrylate, 1,3-butylene glycol dimethacrylate (BGDMA), 1,4-butane diol diacrylate (BDDA), 1,6-hexane diol diacrylate (HDDA), hexanediol dimethacrylate (HDDMA), 1-carboxy-N-methyl-N-di(2-methacryloyloxy-ethyl) methanaminium inner salt (CBMX), neopentylglycol diacrylate (NPGDA), and trimethylolpropane triacrylate (TMPTA), and wherein the photopolymerized zwitterionic hydrogel coating is configured to resist adhesion by biomolecules, cells, tissue or bacteria.

14. The cochlear implant of claim 13, wherein the at least one outer surface of the substrate has uncoated regions, and the uncoated regions and the photopolymerized zwitterionic hydrogel coating form a micropattern on the outer surface of the substrate.

15. The cochlear implant of claim 14, wherein the uncoated regions on the outer surface enable patterned regions of fibrosis.

* * * * *